(12) United States Patent
McMorrow et al.

(10) Patent No.: US 8,715,262 B2
(45) Date of Patent: May 6, 2014

(54) BARRIER FLAP FOR AN ABSORBENT ARTICLE

(75) Inventors: Connie May McMorrow, Menasha, WI (US); Daniel R. Schlinz, Greenville, WI (US); Kylie Bridger, Dulwich Hill (AU); Sara Jane Willie Stabelfeldt, Appleton, WI (US); Patrick Dean Abney, Menasha, WI (US); Daniel Lee Ellingson, Singapore (SG); Sarah A. Funk, Omro, WI (US); Rodney Allen Butler, Galston (AU); Scott Simon Craig Kirby, Wahroonga (AU)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 299 days.

(21) Appl. No.: 13/162,730

(22) Filed: Jun. 17, 2011

(65) Prior Publication Data
US 2012/0323206 A1   Dec. 20, 2012

(51) Int. Cl.
*A61F 13/49*   (2006.01)
*A61F 13/494*   (2006.01)

(52) U.S. Cl.
USPC ............ 604/385.28; 604/385.24; 604/385.25

(58) Field of Classification Search
USPC ..................... 604/385.01, 385.24–385.283
See application file for complete search history.

(56) References Cited

U.S. PATENT DOCUMENTS

| | | | |
|---|---|---|---|
| 4,795,452 A | 1/1989 | Blaney et al. | |
| 4,892,528 A * | 1/1990 | Suzuki et al. | 604/385.27 |
| 4,904,251 A | 2/1990 | Igaue et al. | |
| 5,037,415 A | 8/1991 | Leroy et al. | |
| 5,114,420 A | 5/1992 | Igaue et al. | |
| 5,234,422 A * | 8/1993 | Sneller et al. | 604/385.25 |
| 5,246,432 A * | 9/1993 | Suzuki et al. | 604/385.25 |
| 5,476,458 A | 12/1995 | Glaug et al. | |
| 5,624,426 A | 4/1997 | Roe et al. | |
| 5,769,835 A * | 6/1998 | Fell et al. | 604/385.28 |
| 5,906,603 A | 5/1999 | Roe et al. | |
| 5,931,826 A | 8/1999 | Faulks et al. | |
| 6,159,190 A | 12/2000 | Tanaka et al. | |
| 6,659,993 B2 | 12/2003 | Minato et al. | |
| 6,837,879 B2 | 1/2005 | Kuen et al. | |
| 6,840,929 B2 | 1/2005 | Kurata | |
| 7,118,557 B2 | 10/2006 | Minato et al. | |
| 7,666,175 B2 | 2/2010 | Trennepohl | |
| 2006/0142725 A1 | 6/2006 | Fujikawa et al. | |
| 2010/0191209 A1* | 7/2010 | Nomoto et al. | 604/385.23 |

FOREIGN PATENT DOCUMENTS

| | | |
|---|---|---|
| FR | 2699813 A1 | 7/1994 |
| JP | 3186261 A | 8/1991 |
| JP | 3186262 A | 8/1991 |

(Continued)

OTHER PUBLICATIONS

International Search Report and Written Opinion for PCT/IB2012/052476 dated Dec. 14, 2012; 11 pages.

*Primary Examiner* — Jackie Ho
*Assistant Examiner* — Kathryn E Ditmer
(74) *Attorney, Agent, or Firm* — Armstrong Teasdale LLP

(57) ABSTRACT

An elastic barrier flap for an absorbent article includes a web configured to define a gap and a plurality of elastic members captured by the web. The plurality of elastic members is symmetrically arranged about the gap defined by the web. The web and plurality of elastic members are adapted to inhibit the transverse flow of body exudates released by a wearer of the absorbent article.

20 Claims, 16 Drawing Sheets

(56) References Cited

FOREIGN PATENT DOCUMENTS

| | | | |
|---|---|---|---|
| JP | 4295356 | A | 10/1992 |
| JP | 2000288025 | A1 * | 10/2000 |
| WO | 2004108040 | A1 | 12/2004 |
| WO | 2005060909 | | 7/2005 |
| WO | 2008007247 | A2 | 1/2008 |
| WO | 2009008602 | A1 | 1/2009 |
| WO | WO 2009004940 | A1 * | 1/2009 |
| WO | 2009074898 | | 6/2009 |

* cited by examiner

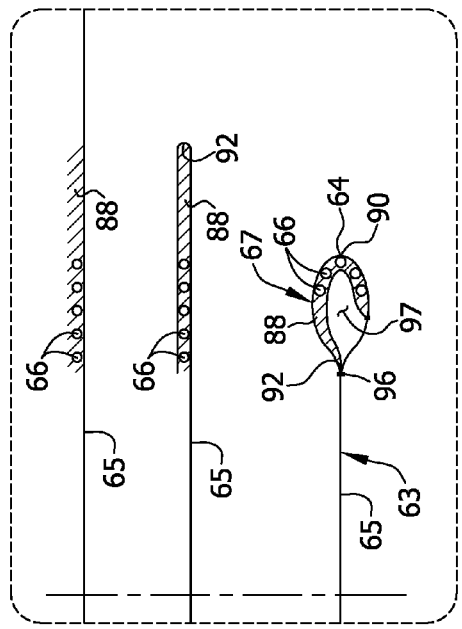
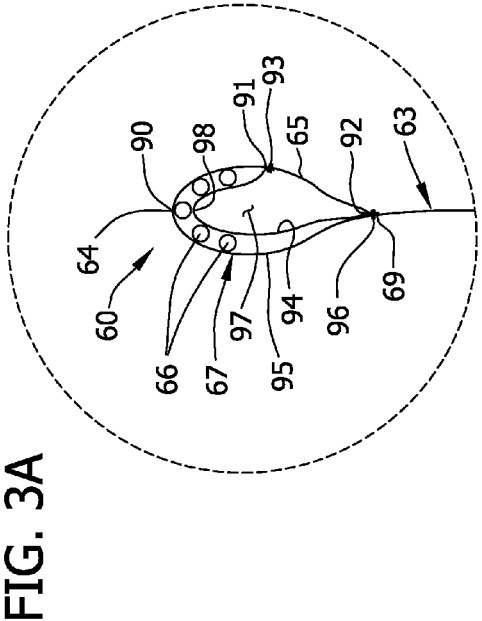
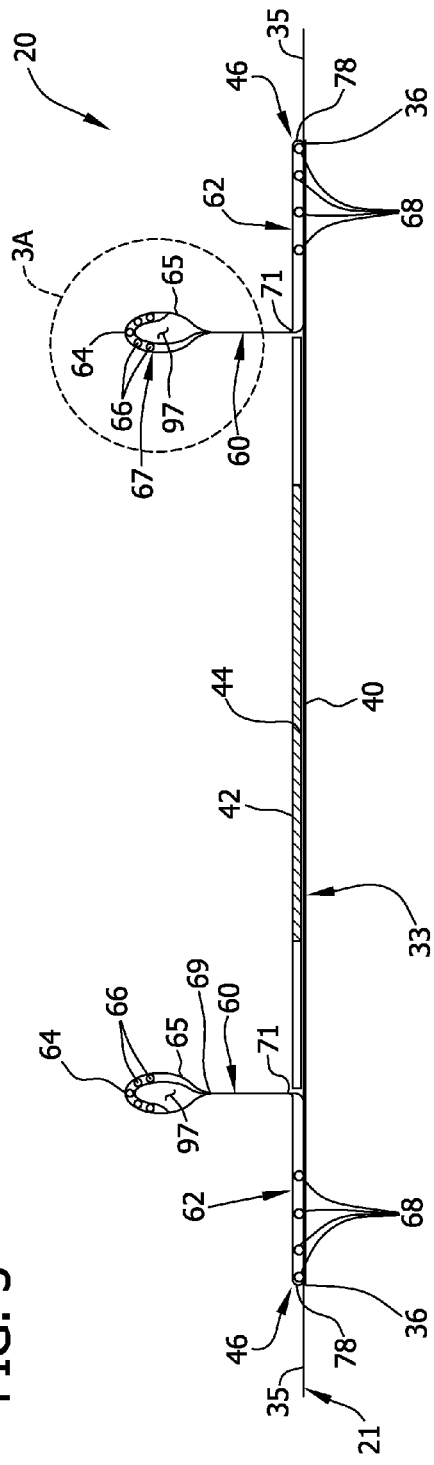

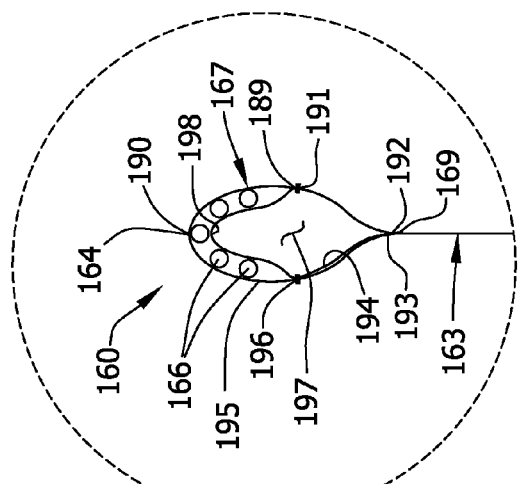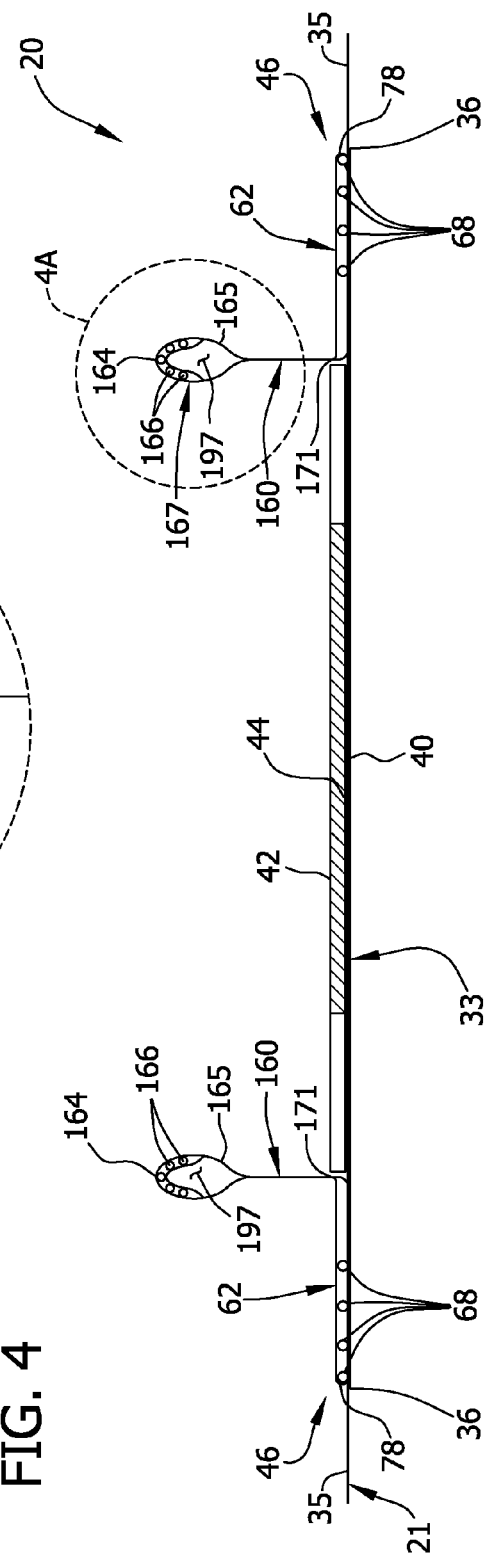

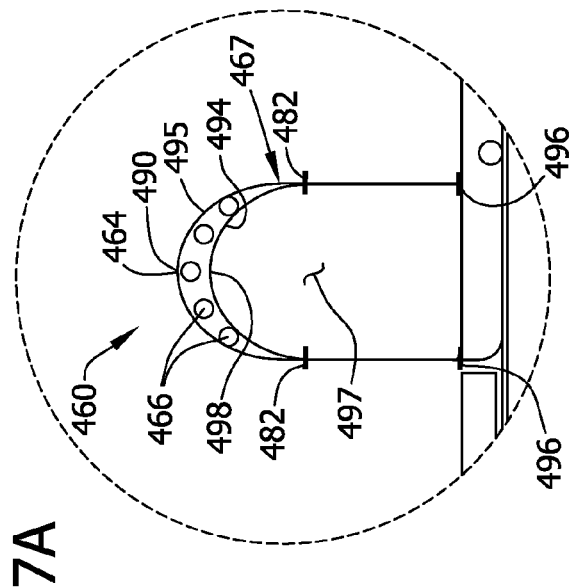
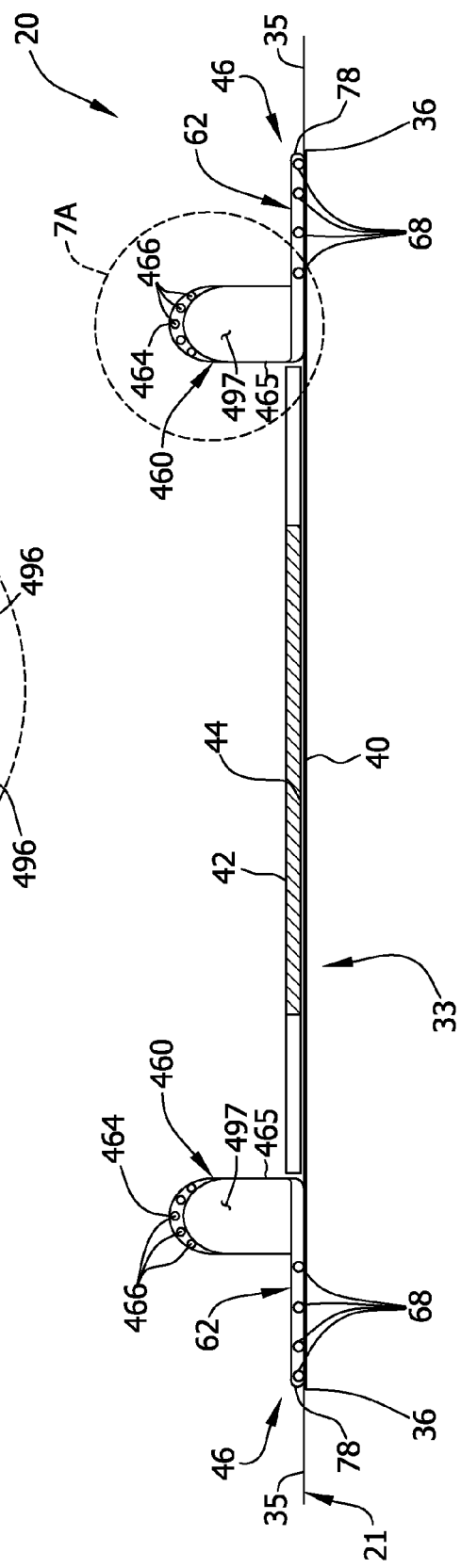
FIG. 7A
FIG. 7

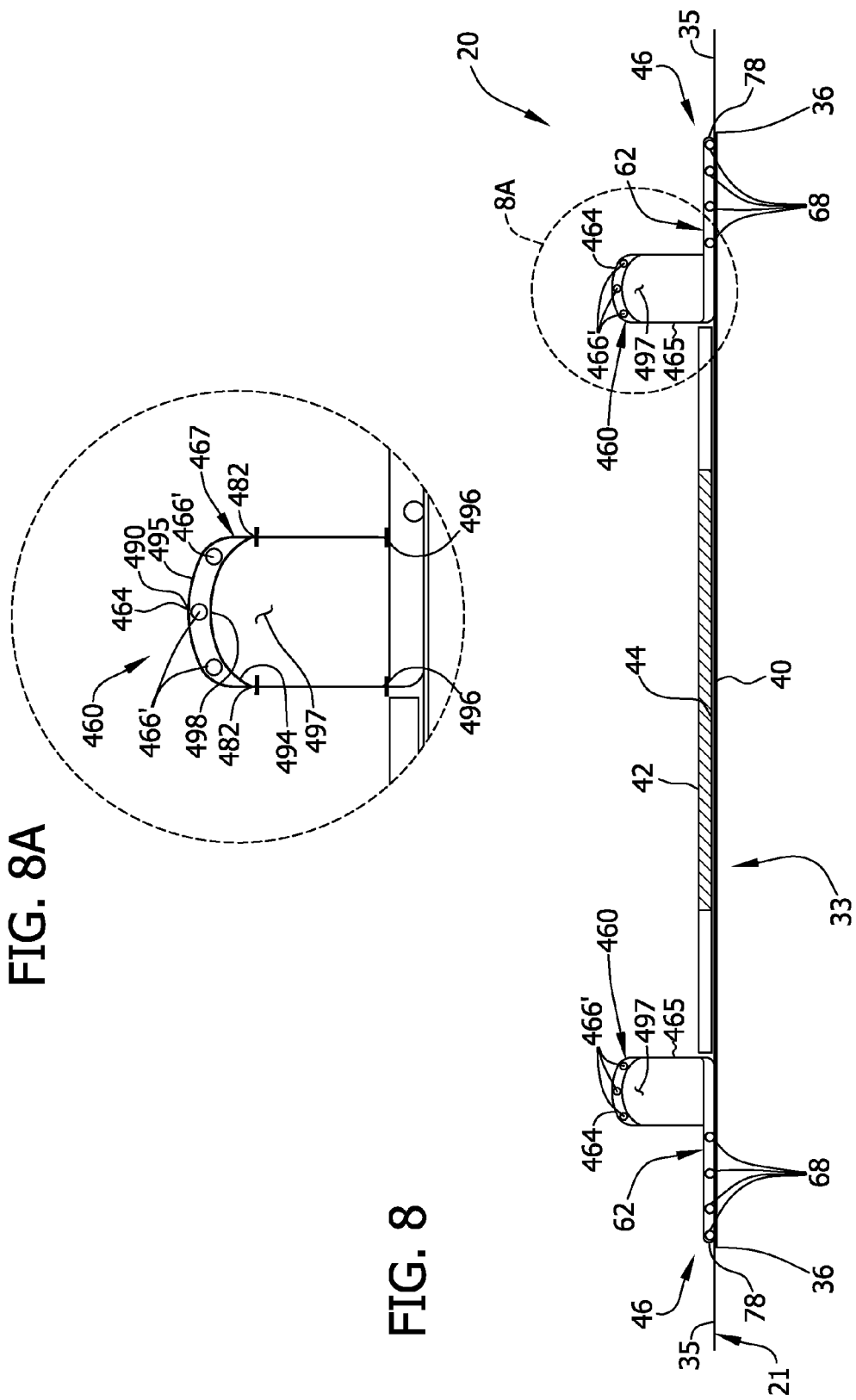

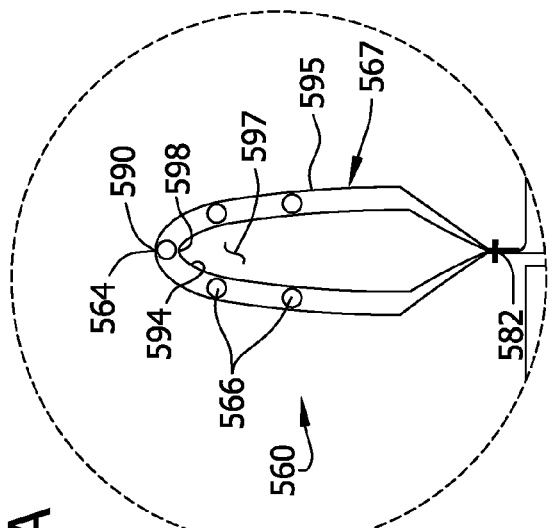
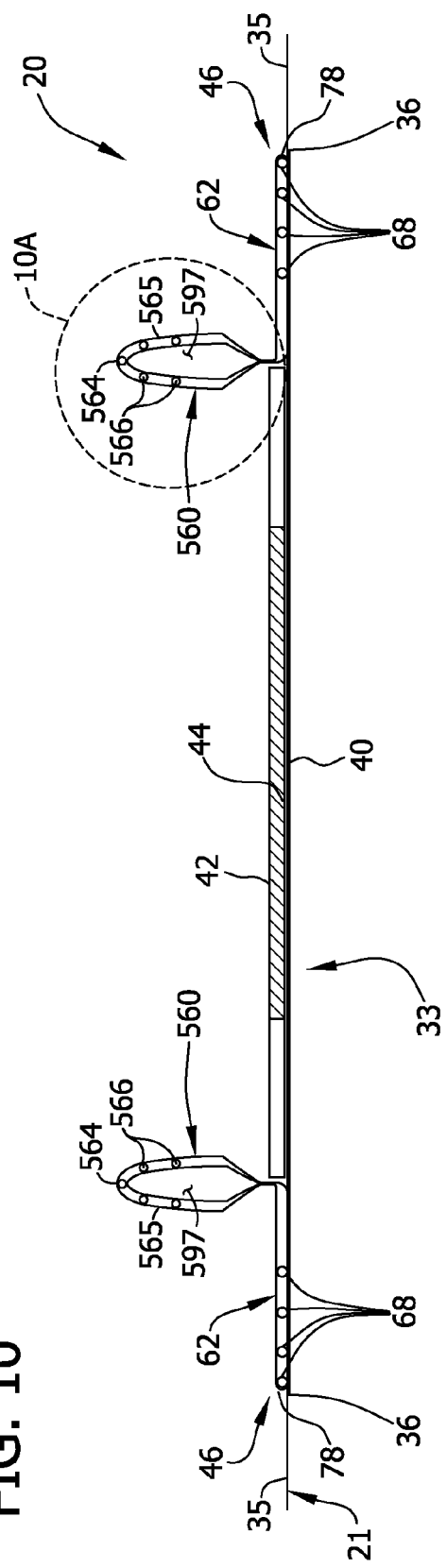
FIG. 10A
FIG. 10

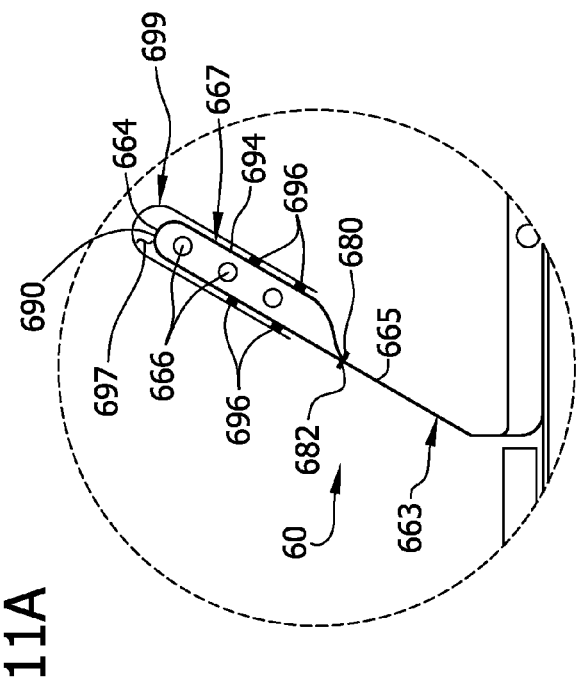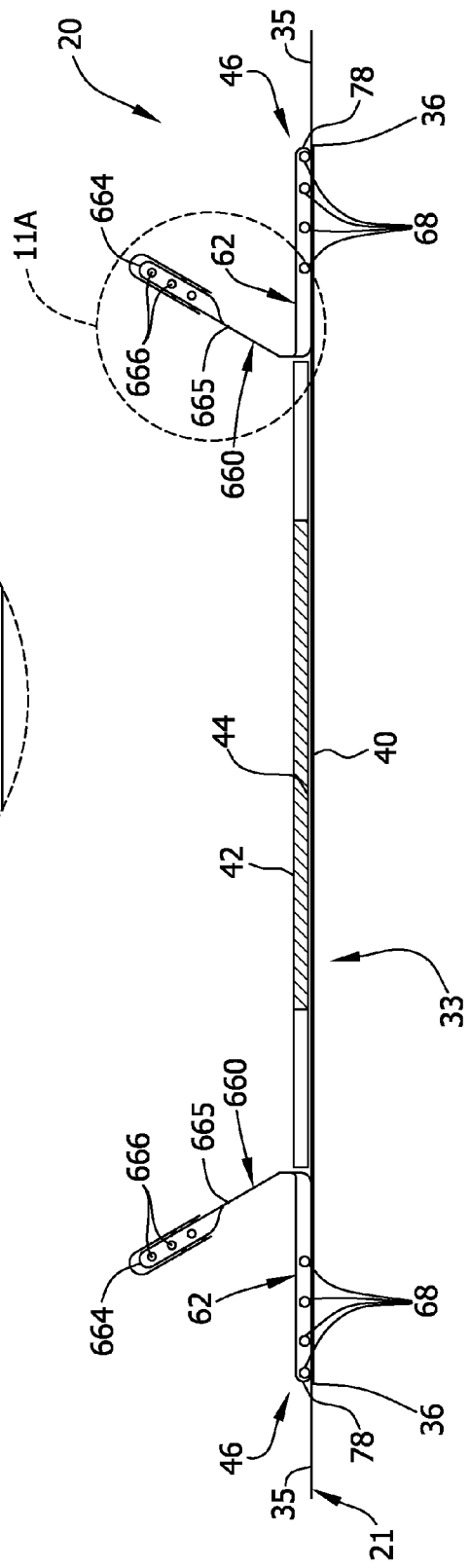

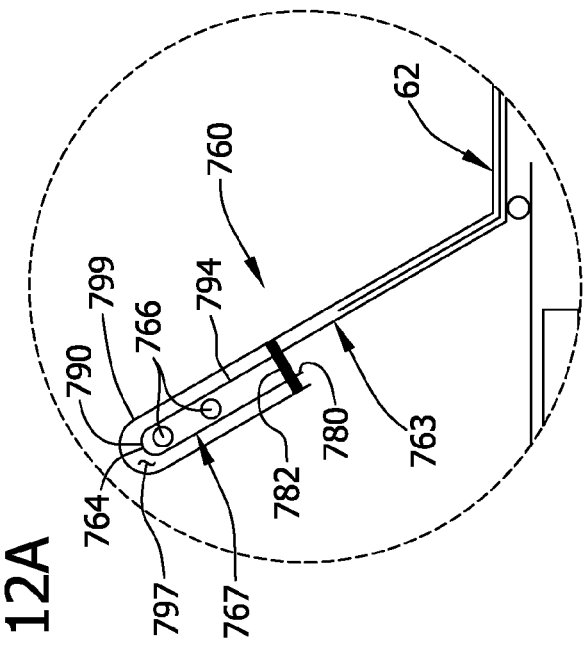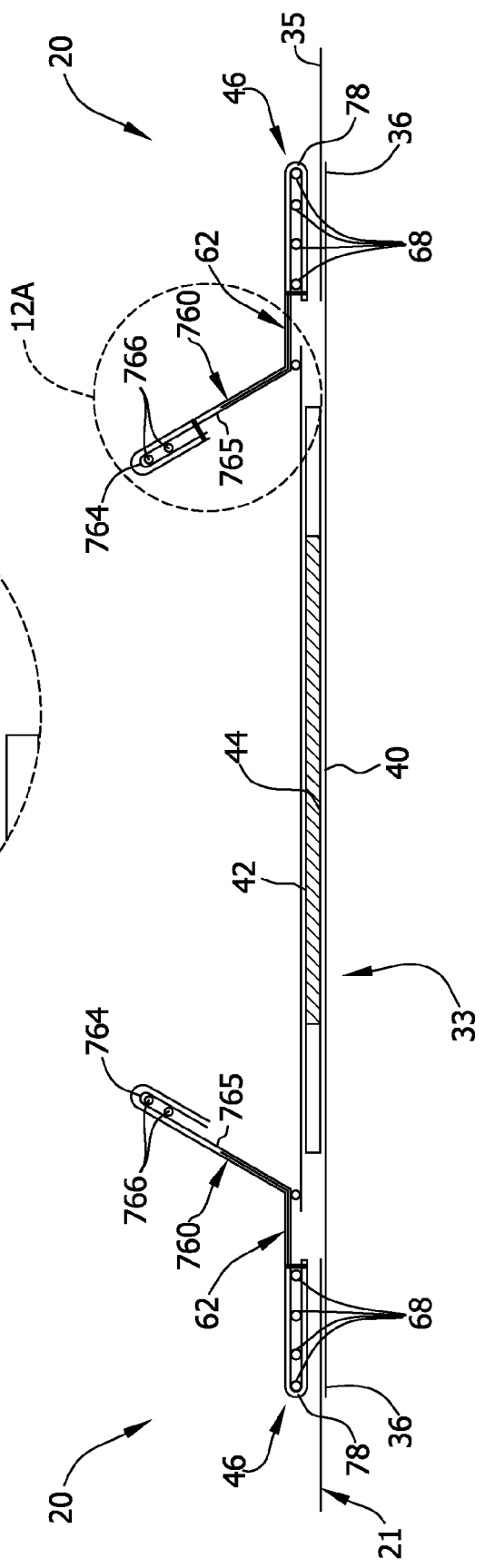

BARRIER FLAP FOR AN ABSORBENT ARTICLE

FIELD

The field of the invention relates generally to disposable absorbent articles and, more particularly, to elastic barrier flaps for absorbent articles and absorbent articles having such barrier flaps.

BACKGROUND

Exemplary disposable absorbent articles include training pants, diapers, incontinence products, disposable underwear, medical garments, absorbent swim wear, and the like. Such absorbent articles typically include an absorbent assembly disposed between an outer cover and a body-side liner. In order to improve the ability of the absorbent articles to absorb and reduce leakage of exudates released by the article wearer, it is known to include elastic barrier flaps and leg cuffs on such articles.

Conventional barrier flaps typically include a single, longitudinally extending flap located on each side of the absorbent assembly of the article. Each of the barrier flaps includes a proximal edge attached to the body-side liner (or some other suitable component of the article) and an elasticized distal edge opposite the proximal edge. Each of the barrier flaps is attached to the article such that the distal edge of the flap is maintained in a generally upright position for contacting the body of a wearer during use. The elasticized distal edges of the barrier flaps provide a seal against the wearer's body to inhibit the transverse flow of exudates.

If the distal edges of the barrier flaps lack sufficient elasticization, the barrier flaps could fail to provide an adequate seal against the wearer's body. The lack of an adequate seal may result in the undesirable leakage of exudates (e.g., runny fecal matter) from the absorbent article. Leakage of exudates past the barrier flaps can result in the unwanted soiling the clothing, bedding, and person.

If the elasticization of the distal edges of the barrier flaps is too great, the barrier flaps can irritate and/or mark the wearer's skin. That is, the wearer's skin can be adversely impacted when the tension and/or elongation of the elastic barrier flaps results in too high of a pressure against the wearer's body when the seal is formed.

As a result, a need remains for barrier flaps that are configured to provide an adequate seal against the wearer's body without irritating and/or marking the wearer's body. Moreover, there is a need for barrier flaps that can be perceived by the wearer and/or caregiver as providing a barrier flap that will inhibit leakage but will also be soft and comfortable against the wearer's body.

SUMMARY

In one aspect, an elastic barrier flap for an absorbent article generally comprises a web configured to define a gap and a plurality of elastic members captured by the web. The plurality of elastic members is symmetrically arranged about the gap defined by the web. The web and plurality of elastic members are adapted to inhibit the transverse flow of body exudates released by a wearer of the absorbent article.

In another aspect, an elastic barrier flap for an absorbent article generally comprises a web having an attached end, an unattached distal end, an inner portion and an outer portion. The inner and outer portions of the web are configured to define a gap. A plurality of elastic members is captured by the web. One of the plurality of elastic members is disposed adjacent the unattached distal end of the web. The other elastic members of the plurality of elastic members are arranged symmetrically about the gap defined by the web and the one of the plurality of elastic members.

In yet another aspect, an elastic barrier flap for providing a barrier to transverse flow of body exudates released by a wearer in an absorbent article generally comprises an outer portion, an inner portion disposed within the outer portion, an air tunnel defined entirely by the inner portion, and a plurality of elastic members captured between the inner and outer portions.

BRIEF DESCRIPTION OF THE DRAWINGS

FIG. 3 is a cross-section of the training pant taken along line 3-3 of FIG. 1 showing one embodiment of a pair of elastic barrier flaps.

FIG. 3A is an enlarged view of a portion of one of the elastic barrier flaps illustrated in FIG. 3.

FIG. 3B is a schematic illustrating a folding process suitable for forming the elastic barrier flaps illustrated in FIG. 3.

FIG. 4 is a cross-section similar to FIG. 3 but showing another embodiment of a pair of elastic barrier flaps.

FIG. 4A is an enlarged view of a portion of one of the elastic barrier flaps illustrated in FIG. 4.

FIG. 7 is a cross-section similar to FIG. 3 but showing another embodiment of a pair of elastic barrier flaps.

FIG. 7A is an enlarged view of a portion of one of the elastic barrier flaps illustrated in FIG. 7.

FIG. 8 is a cross-section similar to FIG. 3 but showing another embodiment of a pair of elastic barrier flaps.

FIG. 8A is an enlarged view of a portion of one of the elastic barrier flaps illustrated in FIG. 8.

FIG. 10 is a cross-section similar to FIG. 3 but showing another embodiment of a pair of elastic barrier flaps.

FIG. 10A is an enlarged view of a portion of one of the elastic barrier flaps illustrated in FIG. 10.

FIG. 11 is a cross-section similar to FIG. 3 but showing yet another embodiment of a pair of elastic barrier flaps.

FIG. 11A is an enlarged view of a portion of one of the elastic barrier flaps illustrated in FIG. 11.

FIG. 12 is a cross-section similar to FIG. 3 but showing still another embodiment of a pair of elastic barrier flaps.

FIG. 12A is an enlarged view of a portion of one of the elastic barrier flaps illustrated in FIG. 12.

Corresponding reference characters indicate corresponding parts throughout the drawings.

DETAILED DESCRIPTION OF THE DRAWINGS

Figure 1:
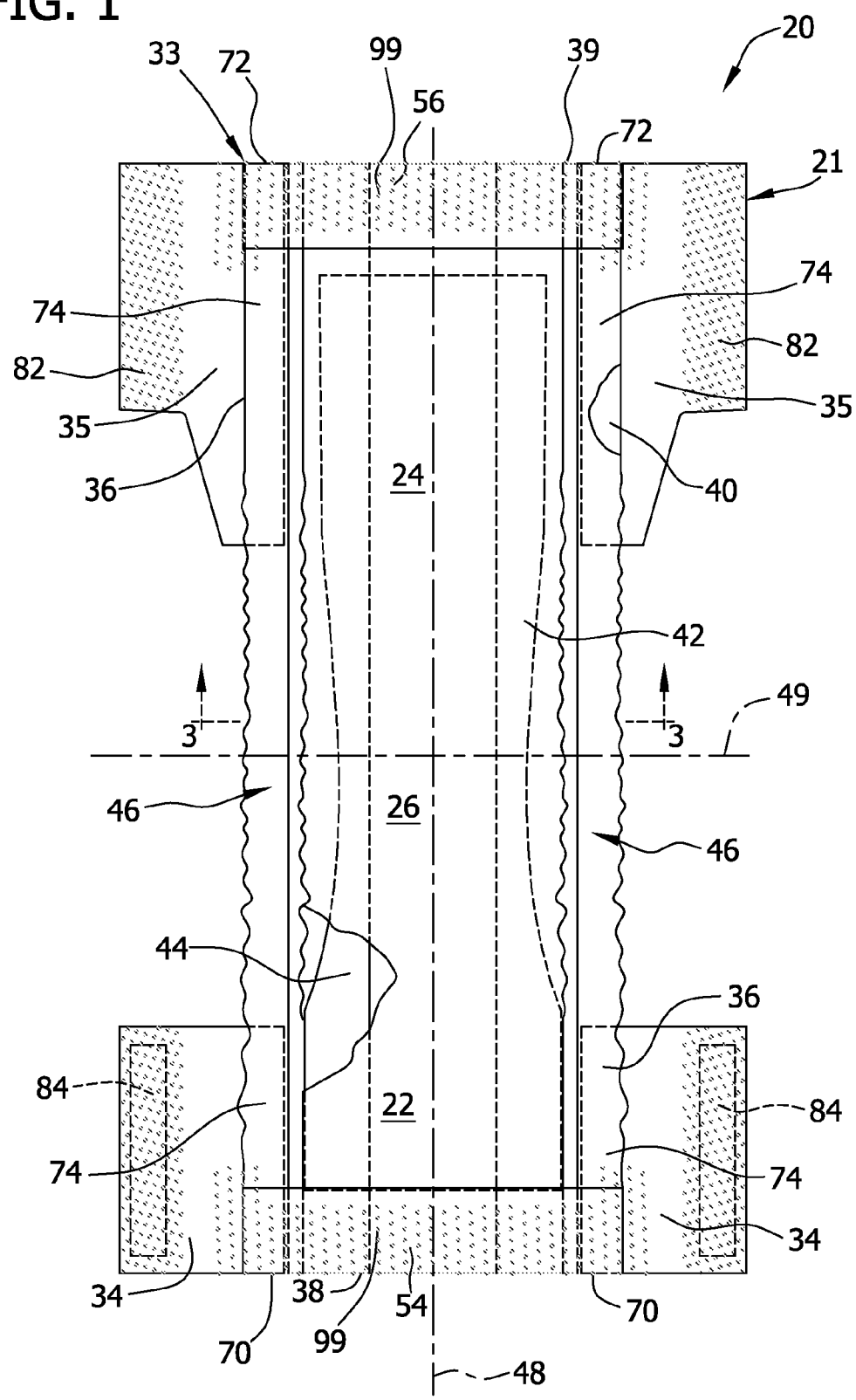
FIG. 1 is a top plan view of one embodiment of an absorbent article in the form of a training pant being in an unfastened, unfolded and laid flat condition, and showing the surface of the training pant that faces a wearer during use, portions of the training pant being removed to show underlying features.

With reference now to the drawings, and in particular to FIG. 1, an absorbent article in the form of a training pant is illustrated in an unfastened, unfolded and laid-flat condition and indicated generally by reference number 20. The training pant 20 comprises a chassis, indicated at 21, having a generally rectangular absorbent structure, indicated at 33, a pair of laterally opposite front side panels 34, and a pair of laterally opposite back side panels 35. For reference purposes, a longitudinal axis 48 and a transverse or lateral axis 49 of the training pant 20 are shown in FIG. 1. It is contemplated that the training pant 20 can have other forms without departing from some aspects of this invention (e.g., a diaper, an incontinence article, disposable underwear, a feminine care article, a medical garment, an absorbent swim wear, and the like).

The absorbent structure 33 of the training pant 20 is configured to contain and/or absorb exudates released by a wearer of the training pant. As seen in FIG. 1, the absorbent structure 33 has a front waist region 22, a back waist region 24, and a crotch region 26 extending between and interconnecting the front and back waist regions. The absorbent structure 33 further includes a pair of side edges 36, a front waist edge 38, and back waist edge 39. The absorbent structure 33 and side panels 34, 35 may comprise separate elements, as shown in FIG. 1, or be integrally formed.

As illustrated in FIGS. 1 and 3, the illustrated absorbent structure 33 comprises an outer cover 40, a body-side liner 42, and an absorbent assembly 44 disposed between the outer cover and the body-side liner. In one suitable embodiment, the outer cover 40 comprises a material that is substantially liquid impermeable, and can be elastic, stretchable, or non-stretchable. The outer cover 40 can be a single layer of liquid impermeable material, but suitably comprises a multi-layered laminate structure in which at least one of the layers is liquid impermeable. For instance, the outer cover 40 can include a liquid permeable outer layer and a liquid impermeable inner layer that are joined together by a laminate adhesive, ultrasonic bonds, thermal bonds, or the like. Suitable laminate adhesives can be applied continuously or intermittently as beads, a spray, parallel swirls, or the like. The liquid permeable outer layer can be any suitable material and desirably one that provides a generally cloth-like texture. The inner layer of the outer cover 40 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 40 when a single layer, inhibits liquid exudates from wetting articles, such as bed sheets and clothing, as well as the wearer and caregiver.

The body-side liner 42 is liquid permeable and overlies the absorbent assembly 44 and outer cover 40. In one suitable embodiment, a width of the body-side liner 42 is less than the width of the outer cover 40. In the illustrated embodiment, for example, the outer cover 40 has a width of approximately 169 millimeters and the body-side liner has a width of approximately 130 millimeters. Thus, longitudinal side portions of the outer cover 40 are uncovered by the body-side liner. In the illustrated embodiment, each of the longitudinal side portions of the outer cover 40 have a width of approximately 19.5 millimeters. It is understood, however, that the body-side liner 42 and the outer cover 40 dimensions other than those illustrated herein. For example, the body-side liner 42 and the outer cover 40 can have substantially the same dimension or the liner 42 can be wider than the outer cover 40.

The body-side liner 42 suitably presents a bodyfacing surface of the training pant 20, which is compliant, soft feeling, and non-irritating to the wearer's skin. Further, the body-side liner 42 may be less hydrophilic than the absorbent assembly 44, to present a relatively dry surface to the wearer, and may be sufficiently porous to be liquid permeable, permitting liquid to readily penetrate through its thickness. A suitable body-side liner 42 may be manufactured from a wide selection of web materials, such as porous foams, reticulated foams, apertured plastic films, natural fibers (i.e., wood or cotton fibers), synthetic fibers (i.e., polyester or polypropylene fibers), or a combination of natural and synthetic fibers. The body-side liner 42 is suitably employed to help isolate the wearer's skin from liquids held in the absorbent assembly 44.

The body-side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body-side liner 42. For example, the body-side liner 42 can be composed of a meltblown or spunbonded web of polyolefin fibers. The body-side liner can also be a bonded-carded web composed of natural and/or synthetic fibers. The body-side liner can be composed of a substantially hydrophobic material, and the hydrophobic material can, optionally, be treated with a surfactant or otherwise processed to impart a desired level of wettability and hydrophilicity. In one suitable embodiment, for example, the body-side liner 42 can be a hydrophobic three-layer nonwoven polypropylene material known as SMS. SMS is an acronym for Spunbond, Meltblown, Spunbond, the process by which the three layers are constructed and then laminated together. One example of an SMS material is described in U.S. Pat. No. 4,041,203 to Brock et al.

The absorbent assembly 44 is generally compressible, conformable, non-irritating to the wearer's skin, and capable of absorbing and retaining liquids and certain body wastes, and may be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Typically, a superabsorbent material is capable of absorbing at least about 15 times its weight in water, and desirably is capable of absorbing more than about 25 times its weight in water. As a general rule, the superabsorbent material is present in the absorbent assembly 44 in an amount of from 0 to about 90 percent weight based on total weight of the absorbent assembly. The absorbent assembly 44 may or may not be wrapped or encompassed by a suitable tissue wrap that may help maintain the integrity and/or shape of the absorbent assembly.

In the illustrated embodiment, a width of the absorbent assembly 44 varies along its length to provide a more comfortable fit to the wearer. More specially, the illustrated absorbent assembly 44 has a width of approximately 115 millimeters in the front waist region 22 of the absorbent structure 33 and approximately 101 millimeters in the back waist region 24 of the absorbent structure. The width of the absorbent assembly 44 tapers inward along its length from the front waist region 22 and the back waist region 24 towards the crotch region 26 to a minimum width of the absorbent assembly 44. The minimum width of the illustrated absorbent assembly 44, which is the crotch region of the absorbent structure 33 is approximately 85 millimeters. It is understood that the absorbent assembly 44 can have any suitable shape and size.

The absorbent structure 33 can also incorporate other materials designed primarily to receive, temporarily store, and/or transport liquid along the mutually facing surface with absorbent assembly 44, thereby maximizing the absorbent capacity of the absorbent assembly. One suitable material is referred to as a surge management layer (not shown) and may be located adjacent the absorbent assembly 44 (e.g., between the absorbent assembly and the liner 42). The surge management layer helps to decelerate and diffuse surges or gushes of liquid that may be rapidly introduced into the absorbent assembly 44. The surge management layer can rapidly accept and temporarily hold the liquid prior to releasing the liquid into the storage or retention portions of the absorbent assembly 44. Examples of suitable surge management layers are described in U.S. Pat. Nos. 5,486,166 and 5,490,846. Other suitable surge management materials are described in U.S. Pat. No. 5,820,973.

As seen in FIG. 1, the front and back side panels 34, 35 are disposed on laterally opposite sides of the absorbent structure 33 in longitudinally spaced relationship with each other. In the illustrated embodiment, the front and back side panels 34, 35 are permanently bonded along seams to the absorbent structure 33 in the respective front and back waist regions 22, 24. More specifically, each of the front and back side panels 34, 35 are sandwiched between the outer cover 40 and the body-side liner 42 permanently bonded to both the outer cover and the body-side liner. The front side panels 34 extend transversely outward beyond the side edges 36 of the absorbent structure 33 in the front waist region 22, and the back side panels 35 extend transversely outward beyond the side edges of the absorbent structure in the back waist region 24.

The front and back side panels 34, 35 may be bonded to the absorbent structure 33 using attachment means known to those skilled in the art such as adhesive, thermal or ultrasonic bonding. In the illustrated embodiment, for example, the front and back side panels 34, 35 are adhesively bonded to both the outer cover 40 and the body-side liner 42. As mentioned above, the front and back side panels 34, 35 can be formed as an integral portion of a component of the absorbent structure 33. For example, the front and back side panels can comprise a generally wider portion of the outer cover 40 and/or the body-side liner 42.

In one suitable embodiment, the front and back side panels 34, 35 comprise an elastic material capable of stretching in a direction generally parallel to the transverse axis 49 of the training pant 20. Suitable elastic materials, as well as one process of incorporating elastic side panels into training pant, are described in U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.

In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al. Alternatively, the side panel material may comprise other woven or nonwoven materials, such as those described above as being suitable for the outer cover 40 or body-side liner 42, mechanically prestrained composites, or stretchable but inelastic materials.

The illustrated training pant 20 includes a fastening element for refastenably securing the training pant about a waist of the wearer. It is understood, however, that the front and back side panels 34, 35 can be permanently bonded together. The illustrated fastening element includes first fastening components 84 adapted for refastenable engagement to corresponding second fastening components 82. In the illustrated embodiment, the first fastening components 84 comprise a plurality of projecting engaging elements. The engaging elements of the first fastening components 84 are adapted to repeatedly engage and disengage engaging elements of the second fastening components 82.

The fastening components 84, 82 can comprise separate elements bonded to the side panels 34, 35, or they may be integrally formed with the side panels. In the illustrated embodiment, for example, the first fastening components 84 are formed separate from the front side panels 34 and bonded thereto. The second fastening components 82, on the other hand, are integrally formed with the back side panels 35. The first fastening components 84 can be bonded to the respective front side panels 34 by any means known to those skilled in the art such as adhesive bonds, ultrasonic bonds or thermal bonds.

The fastening components 84, 82 can comprise any refastenable fasteners suitable for absorbent articles, such as adhesive fasteners, cohesive fasteners, mechanical fasteners, or the like. In the illustrated embodiment, the fastening components 84, 82 comprise mechanical fastening elements. Suitable mechanical fastening elements can be provided by interlocking geometric shaped materials, such as hooks, loops, tubular elements, mushrooms, arrowheads, balls on wall elements, male and female mating components, buckles, snaps, or the like.

In the illustrated embodiment, the first fastening components 84 comprise hook fasteners and the second fastening components 82 comprise complementary loop fasteners. In another suitable embodiment, the first fastening components 84 comprise loop fasteners and the second fastening components 82 comprise complementary hook fasteners. Alternatively, the fastening components 84, 82 may comprise interlocking similar surface fasteners, adhesive or cohesive fastening elements such as an adhesive fastener and an adhesive-receptive landing zone or material; or the like.

Figure 2:
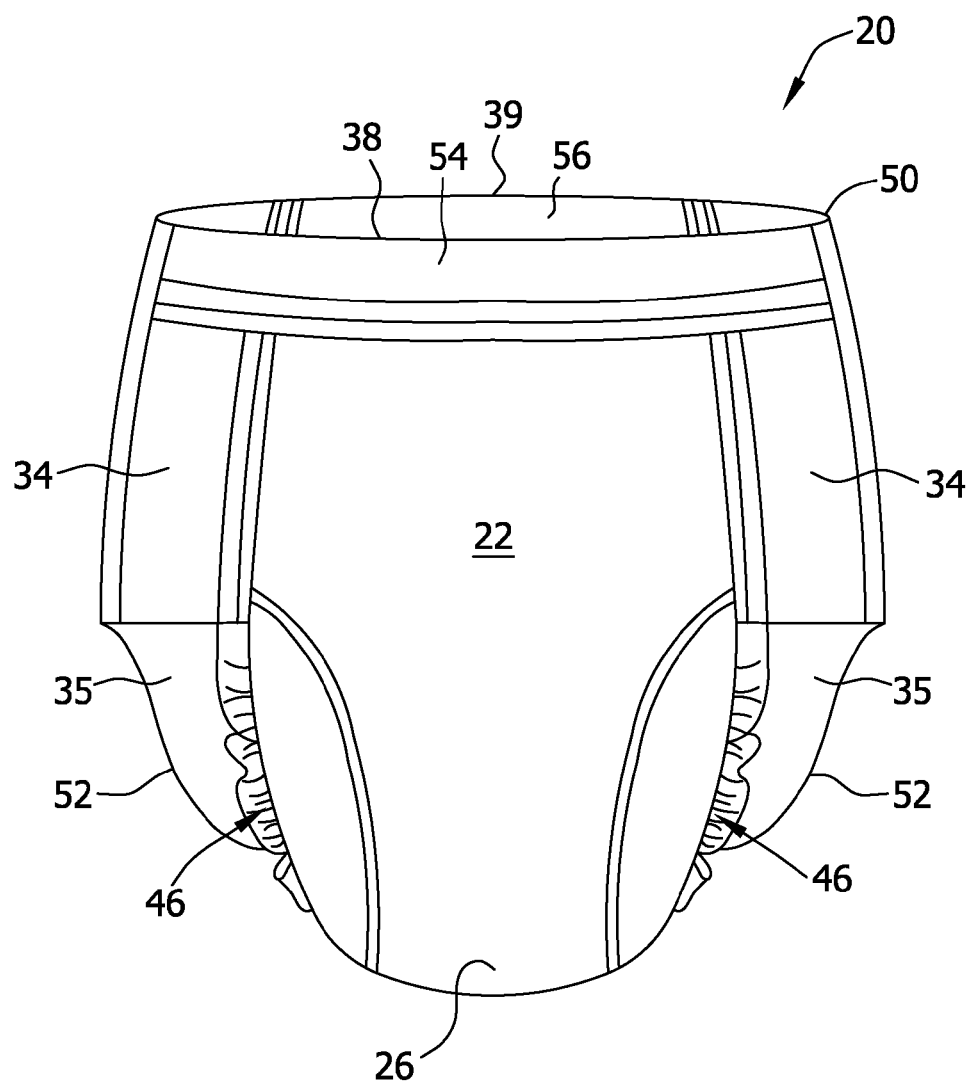
FIG. 2 is a front perspective of the training pant of FIG. 1 in a wear configuration of the training pant.

In a ready-to-wear, three dimensional configuration of the training pant 20, which is illustrated in FIG. 2, the front and back side panels 34, 35 are secured together to define a three-dimensional pant configuration having a waist opening 50 and a pair of leg openings 52. The front waist region 22 comprises the portion of the training pant which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The front and back side panels 34, 35 define the portions of the training pant 20 which, when worn, are positioned on the hips of the wearer. The waist edges 38, 39 of the absorbent chassis 21 are configured to encircle the waist of the wearer when worn and together define the waist opening 50.

As seen in FIG. 2, in the ready-to-wear, three dimensional configuration of the training pant 20, the back side panels 35 overlaps the front side panels 34 when the first fastening component 84 is engaged with the second fastening component 82. It is understood, however, that the training pant 20 may instead be configured so that the front side panels 34 overlap the back side panels 35.

With reference now to FIGS. 1 and 3, the illustrated training pant 20 includes a pair of spaced-apart leg and elastic barrier flap composites, indicated generally at 46. Each of the leg and elastic barrier flap composites 46 has a barrier flap portion, indicated generally at 60, and a gasket portion, indicated generally at 62. In the embodiment illustrated in FIGS. 1-3, the leg and elastic barrier flap composites 46 are formed as a single-piece of material and bonded to the chassis 21 of the training pant 20. It is understood, however, that the leg and elastic barrier flap composites 46 can be formed from two or more pieces of material. That is, the barrier flap portion 60 can be formed separately from the gasket portion 62.

In the illustrated embodiment, the leg and elastic barrier flap composites 46 extend longitudinally along the entire length of the absorbent structure 33. It is contemplated that the leg and elastic barrier flap composites 46 can extend less than the entire length of the absorbent structure 33. It is also contemplated that one of the barrier flap portion 60 or the gasket portion 62 can extend less than the entire length of the absorbent structure 33.

The barrier flap portion 60 of each of the leg and elastic barrier flap composites 46 provides a barrier to the transverse flow of body exudates released by the wearer. More specifically, each of the barrier flap portions 60 assumes an upright configuration during use to define an unattached, distal edge 64 in at least the crotch region 26 of the absorbent structure 33 of the training pant 20 to form a seal against the wearer's body. The unattached, distal edge 64 of the barrier flap portion 60 is illustrated in the upright configuration in FIGS. 3 and 3A. It has been found that barrier flap portions 60 can be made more comfortable for the wearer, or at least perceived to be more comfortable, by increasing the width (i.e., the lateral extent) of the barrier flap portions at or near the unattached, distal edge 64, which is the part of the barrier flap portion that contacts the wearer during use.

In the illustrated embodiment, the barrier flap portions 60 of the leg and elastic barrier flap composites 46 are generally aligned with the lateral side edges of the absorbent assembly 44 in at least the crotch region of the absorbent structure 33. It is contemplated, however, that the barrier flap portions 60 can be spaced inward or outward from the respective lateral side edge of the absorbent assembly 44.

The barrier flap portions 60 of the illustrated embodiment lie generally flat in at least a portion of the front waist region 22 and the back wait region 24 of the absorbent structure 33 during use of the training pant 20. Thus, in the front and back waist regions 22, 24 of the absorbent structure 33, the barrier flap portions 60 lie in generally face-to-face relationship with the body-side liner 42. In addition, the barrier flap portions 60 are bonded or otherwise fixed to the body-side liner 42 in at least a portion of the front and back waist regions 22, 24. It is understood, however, that the barrier flap portions 60 can be adapted to assume an upright configuration along substantially their entire length.

As seen in FIGS. 3 and 3A, each of the barrier flap portions 60 of the leg and elastic barrier flap composites 46 comprises a web 65 and a plurality of elastic members 66 (five elastic members being illustrated in FIGS. 3 and 3A) operatively joined thereto. In this embodiment, the web 65 is a single piece of material defining a wall element, indicated generally at 63, and a tubular element, indicated generally at 67, extending upward from an upper end 69 of the wall element. In the illustrated embodiment, the other end or a lower end 71 of the wall element is affixed to the gasket portion 62 of the leg and elastic barrier flap composites 46. It is contemplated, however, that the lower end 71 of the wall element 63 can be affixed to the body-side liner 42 or outer cover 40 of the chassis 21 of the training pant 20.

As best illustrated in FIG. 3A, the tubular element 67 includes an inner portion 94 and an outer portion 95. The portion of the web 65 defining the outer portion 95 of the tubular element 67 extends upward from the wall element 63 and is folded downward about a first fold line 90, which generally defines the unattached, distal edge 64 of the barrier flap portion 60. As used herein, "fold line" means a line about which the web changes direction. The web 65 is then folded inward and upward about a second fold line 92 and is bonded to itself via a bond point 96 generally at the second fold line 92. As see in FIG. 3A, the bond point 96 is located generally adjacent the upper end 69 of the wall element 63.

The inner portion 94 of the web 65 extends upward from the bond point 96 and folded downward about a third fold line 98, which is generally aligned with and spaced below the first fold line 90. A terminus 91 of the inner portion 94 of the tubular element 67 is bonded to the outer portion 95 of the tubular element web at a point bond 93. It is contemplated that the web 65 can be made from more than one-piece of material. For example, the inner portion 94 and/or the outer portion 95 of the web 65 can be formed as a separate piece and bonded to other portions of the web.

In one suitable embodiment, the web 65 is made from a lightweight nonwoven laminate. Such suitable laminates are described in U.S. Pat. No. 5,492,751 to Butt, Sr. et al., which is hereby incorporated by reference in its entirety. In one example, the laminate includes at least one fine fiber component layer and at least one continuous filament layer.

The fine fiber layer includes fibers having an average diameter in the range of up to about 10 microns and a basis weight in the range of from about 1.5 gsm to about 26 gsm. Suitably, the average fine fiber diameter will be in the range of up to about 5 microns, and the fine fiber web basis weight will be in the range of from about 1.5 to about 10 gsm.

The continuous filament web has filaments with an average diameter in the range of from about 12 microns to about 22 microns and a basis weight in the range of from about 10 gsm to about 30 gsm. Suitably, the continuous filaments have an average diameter in the range of from about 12 microns to about 18 microns and a basis weight in the range of from about 10 gsm to about 20 gsm.

The layers of the laminate are bonded together intermittently for a total basis weight not to exceed about 55 gsm and with the amount of fine fibers based on the laminate weight of at least 5%. The laminate basis weight is suitably within the range of up to about 20 gsm and the fine fibers constitute a low proportion of the laminate in the range of about 5% to about 25%.

With reference still to FIG. 3A, each of the elastic members 66 are captured by or otherwise enclosed within the web 65. In the illustrated embodiment, the elastic members 66 are captured between the inner and outer portions 94, 95 of the tubular element 67. As seen in FIGS. 3 and 3A, one of the elastic members 66 is disposed generally adjacent the unattached, distal edge 64 of the barrier flap portion 60 and between the first and third fold lines 90, 98. The other elastic members 66 are positioned generally symmetrically downward and outward from the one adjacent the unattached, distal edge 64 in a generally inverse U-shaped pattern. The web 65 and the elastic members 66 cooperatively define a gap 97, which provides an air pocket (or air tunnel) within the barrier flap portion 60 of the leg and elastic barrier flap composites 46.

In the illustrated embodiment, the gap 97 extends at least through the crotch region 26 of the absorbent structure 33. More specifically, the gap 97 extends between the parts of the barrier flap portion 60 bonded in the front and back waist regions 22, 24 of the training pant 20. In other words, the gap 97 is formed in the parts of the barrier flap portion having the unattached, distal edge 64.

As a result, the web 65 and elastic member 66 configuration illustrated in FIGS. 3 and 3A provides a barrier flap portion 60 that is soft and comfortable for the wearer of the training pant 20. More specifically, the illustrated web 65 and elastic member 66 configuration inhibits red-marking of the wearer's skin. Moreover, the illustrated leg and elastic barrier flap composite 46 provides a barrier flap portion 60 that looks soft (e.g., like a cushion) giving the wearer and/or the wearer's caregiver the perception that the training pant 20 is soft and comfortable to wear.

In the illustrated embodiment, the elastic members 66 are adhesively bonded to the inner and outer portions 94, 95 of the tubular element 67 of the barrier flap portions 60 of the leg and elastic barrier flap composites 46. It is understood, however, that the elastic members 66 can be operatively joined to the barrier flap portions 60 in any suitable manner as is well known in the art. It is also understood that the barrier flap portions 60 can include more or fewer elastic members 66 and that the elastic members can be any suitable elastomeric material (e.g., strands, ribbons).

In the illustrated embodiment, for example, each of the elastic members 66 is an elastic strand having a decitex of about 470. It is understood, however, that one or more of the elastic strands can have a different (i.e., greater or lesser) decitex than about 470. In the illustrated embodiment, the elastic strands are spaced from each other by about the same distance. It is understood, however, that the spacing between elastic strands can be varied. That is, the spacing between two of the elastic strands can be different than the spacing between two different elastic strands.

FIG. 3B schematically illustrates one suitable folding process for forming the elastic barrier flaps 60 illustrated in FIG. 3. As seen therein, the plurality of elastic members 66 are adhered to the web 65, which is laid generally flat, with adhesive 88. The adhesive 88 extends outward beyond the plurality of elastic members 66. In the illustrated embodiment, for example, about half of the adhesive 88 adheres the plurality of elastic members 66 to the web 65 and the half of adhesive is located outward beyond the plurality of elastic members 66. The web 65 is then folded about a fold line (e.g., the second fold line 92) such that a portion of the web overlies and is adhered by the adhesive 88.

The web 65 is folded again about another fold line (e.g., about the first fold line 90 and the third fold line 98) such that one of the plurality of elastic members 66 is located generally adjacent the unattached, distal edge 64 and the other elastic members are symmetrically aligned in a generally inverse U-shaped pattern. The portion of the web 65 adjacent the second fold line 92 is bonded to the web at bond point 96. Thus, the web 65, which is a single piece of material, defines both the wall element 63 and the tubular element 67 extending upward from the upper end 69 of the wall element.

During use, the gasket portions 62 of the leg and elastic barrier flap composites 46 seal against the legs of the wearer when the wearer's legs are received in the leg openings 52 of the training pant 20. In the illustrated embodiment, the gasket portions 62 are generally aligned with the side edges 36 of the absorbent structure 33 (which is defined by the outer cover 40) and extend longitudinally along the entire length of the absorbent structure. It is contemplated, however, that the gasket portions 62 can be spaced inward or outward from the respective side edge 36 of the absorbent structure 33. It is also contemplated that the gasket portions 62 can extend less than the entire length of the absorbent structure 33.

As seen in FIG. 3, each of the gasket portions 62 of the leg and elastic barrier flap composites 46 comprises four elastic members 68 operatively joined thereto. In the illustrated embodiment, the elastic members 68 are adhesively bonded to the gasket portions 62 of the leg and elastic barrier flap composites 46 but it is understood that the elastic members can be operatively joined to the gasket portions in any suitable manner as is well known in the art. It is also understood that the gasket portions 62 of the leg and elastic barrier flap composites 46 can include more or fewer elastic members 68 and that the elastic members can be made of any suitable elastomeric materials (e.g., strands, ribbons). In the illustrated embodiment, for example, the elastic members 68 are elastic strands having a decitex of about 470.

As mentioned above, the gasket portions 62 of the leg and elastic barrier flap composites 46 form a gasket (i.e., sealingly engage) with each the legs of the wearer when the wearer's legs are received through the respective leg openings 52. In addition, the gasket portions 62 extend into operative engagement with the respective front and back side panels 34, 35, which create fully encircling leg gaskets, which significantly inhibit leakage.

The presence or noticeability of the barrier flap portions 60 and/or the gasket portions 62 of the leg and elastic barrier flap composites 46 can be enhanced by providing graphics and/or texturing (not shown). In one suitable embodiment, the graphics and/or texturing is provided to increase the noticeability of the softness and comfort of the barrier flap portions 60.

The elastic members 66, 68 of the leg and elastic barrier flap composites 46 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate.

As seen in FIG. 1, each of the leg and elastic barrier flap composites 46 has a front edge 70 and a back edge 72. In the illustrated embodiment, the front edge 70 is generally coterminous with the front waist edge 38 of the absorbent structure 33 and the back waist edge 39 is generally coterminous with the back waist edge. It is contemplated, however, that the front and back edges 70, 72 of the leg and elastic barrier flap composites 46 can be spaced inward from the respective front and back waist edges 38, 39 of the absorbent structure 33.

Each of the leg and elastic barrier flap composites 46 include deadened portions 74 adjacent to both the front edge 70 and back edge 72 thereof. The deadened portions 74 are portions of the leg and elastic barrier flap composites 46 wherein the elastic members 66 of the barrier flap portions 60 and the elastic members 68 of the gasket portions 62 have been rendered inelastic. As seen in FIG. 1, the deadened portions 74 of the leg and elastic barrier flap composites located in the back waist region 24 of the absorbent structure 33 extend further from the base waist edge 39 than do the deadened portions located in the front waist region 22 of the absorbent structure. In other words, the deadened portions 74 are longer in the back waist region 24 than they are in the front waist region 22. It is understood, however, that the deadened portion in the front waist region 22 can have the same length as the deadened portions in the back waist region 24. It is also understood that the deadened portion in the front waist region 22 can be longer than the deadened portions in the back waist region 24.

In one suitable embodiment, outer side edges 78 of each of the leg and elastic barrier flap composites 46, which are defined by the gasket portions 62, are aligned with the respective side edge 36 of the outer cover 40. In other words, the outer side edges 78 of the leg and elastic barrier flap composites 46 and the side edges 36 of the outer cover 40 are coterminous (FIG. 3). This configuration creates a cuff-like appearance at the leg openings 52 which can be perceives as being underwear-like. In another suitable embodiment, the outer side edges 78 of the leg and elastic barrier flap composites 46 can extend outward beyond the respective sides edge 36 of the outer cover 40.

As seen in FIG. 1, the training pant 20 includes a front waist elastic member 54, and a back waist elastic member 56. The waist elastic members 54, 56 can be formed of any suitable elastic material. Suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In the illustrated embodiment, both the front and back waist elastic members 54, 56 are generally rectangular. It is understood, however, that the front waist elastic member 54 and/or the back waist elastic member 56 can be of other suitable shapes and sizes.

In one suitable embodiment, the front and back waist elastic members 54, 56 are both adhesively bonded and point bonded to the absorbent structure 33. In the illustrated embodiment, for example, the front and back waist elastic members 54, 56 are adhesively bonded and point bonded to the inner surface of the absorbent structure 33 (i.e., the surface of the absorbent structure that faces the wearer during use of the training pant 20). More specifically, the front and back waist elastic members 54, 56 are adhesively bonded to the body-side liner 42 and the deadened portions 74 of the leg and elastic barrier flap composites 46.

The front and back waist elastic members 54, 56 are also point bonded to the body-side liner 42, the outer cover 40, and the deadened portions 74 of the leg and elastic barrier flap composites 46 via a plurality of point bonds 99. As seen in FIG. 1, the point bonds 99 are generally aligned in longitudinally extending rows with each of the rows being generally uniformly spaced apart, which provides uniform gathers in the front and back waist elastic members 54, 56. In one suitable embodiment, the spacing between the rows can be within a range between about 3 millimeters and about 12 millimeters. In the illustrated embodiment, for example, the spacing between the longitudinally extending rows of point bonds 99 is about 5 millimeters. It is understood that the spacing between the longitudinally extending rows can differ.

In one suitable embodiment, the spacing between the point bonds 99 within the longitudinal extending rows is less than about 10 millimeters. For example, the spacing between point bonds 99 within the longitudinal extending rows in the illustrated embodiment is about 5 millimeters. It is understood that the spacing between point bonds 99 within the longitudinally extending rows can differ.

As seen in FIG. 1, the illustrated bond points 96 are generally circular and have a diameter of less than about 10 millimeters and suitably, between about 0.5 millimeters and about 3 millimeters. In the illustrated embodiment, for example, the bond points 96 have a diameter of approximately 1 millimeter. It is understood, however, that the bond points can have any suitable size or shape. For example, the diameter of the point bonds 99 can be between approximately 0.5 millimeters and about 10 millimeters.

In the illustrated embodiment, the front waist elastic member 54 is bonded to the absorbent structure 33 in substantially the same manner as the back waist elastic member 56. It is contemplated, however, that the front waist elastic member 54 and back waist elastic member 56 can be bonded to the absorbent structure 33 in different manners. It is also contemplated that the front waist elastic member 54 and/or the back waist elastic member 56 can be bonded to the absorbent structure 33 using one of adhesive bonding or point bonding.

Another suitable embodiment of a barrier flap portion 160 of the leg and elastic barrier flap composites 46 is illustrated in FIGS. 4 and 4A. The barrier flap portion 160 provides a barrier to the transverse flow of body exudates released by the wearer. More specifically, each of the barrier flap portions 160 assumes an upright configuration during use to define an unattached edge 164 in at least the crotch region 26 of the absorbent structure 33 of the training pant 20 to form a seal against the wearer's body.

As seen in FIGS. 4 and 4A, each of the barrier flap portions 160 of the leg and elastic barrier flap composites 46 comprises a web 165 and a plurality of elastic members 166 (five elastic members being illustrated in FIGS. 4 and 4A) operatively joined thereto. In this embodiment, the web 165 is a single piece of material defining a wall element, indicated generally at 163, and a tubular element, indicated generally at 167, extending upward from an upper end 169 of the wall element. In the illustrated embodiment, the other end or a lower end 171 of the wall element is affixed to the gasket portion 62 of the leg and elastic barrier flap composites 46. It is contemplated, however, that the lower end 171 of the wall element 163 can be affixed to the body-side liner 42 or outer cover 40 of the chassis 21 of the training pant 20.

As best illustrated in FIG. 4A, the tubular element 167 includes an inner portion 194 and an outer portion 195. The portion of the web 165 defining the outer portion 195 of the tubular element 167 extends upward from the wall element 163 and is folded downward about a first fold line 190, which generally defines the unattached, distal edge 164 of the barrier flap portion 160. The web 165 is then folded inward and upward about a second fold line 192 and is bonded to itself via a bond point 196 generally at the second fold line 192. As see in FIG. 4A, the bond point 196 is located generally adjacent the upper end 169 of the wall element 163.

The inner portion 194 of the web 165 extends upward from the bond point 193 and is bonded to the outer portion 195 at a bond point 189. From the bond point 197, the inner portion 194 of the web 165 extends further upward and is folded downward about a third fold line 198, which is generally aligned with and spaced below the first fold line 190. A terminus 191 of the inner portion 194 of the tubular element 167 is bonded to the outer portion 195 of the tubular element web at a point bond 193. It is contemplated that the web 165 can be made from more than one-piece of material. For example, the inner portion 194 and/or the outer portion 195 of the web 65 can be formed as a separate piece and bonded to other portions of the web.

With reference still to FIG. 4A, each of the elastic members 166 are captured by or otherwise enclosed within the web 165. In the illustrated embodiment, the elastic members 166 are captured between the inner and outer portions 194, 195 of the tubular element 167. As seen in FIGS. 4 and 4A, one of the elastic members 166 is disposed generally adjacent the unattached, distal edge 164 of the barrier flap portion 160 and between the first and third fold lines 190, 198. The other elastic members 166 are positioned generally symmetrically downward and outward from the one adjacent the unattached, distal edge 164 in a generally inverse U-shaped pattern. The web 165 and the elastic members 166 cooperatively define a gap 197, which provides an air pocket (or air tunnel) within the barrier flap portion 160 of the leg and elastic barrier flap composites 46.

In the illustrated embodiment, the gap 197 extends at least through the crotch region 26 of the absorbent structure 33. More specifically, the gap 197 extends between the parts of the barrier flap portion 160 bonded in the front and back waist regions 22, 24 of the training pant 20. In other words, the gap 197 is formed in the parts of the barrier flap portion having the unattached, distal edge 164.

As a result, the web 165 and elastic member 166 configuration illustrated in FIGS. 4 and 4A provides a barrier flap portion 160 that is soft and comfortable for the wearer of the training pant 20. More specifically, the illustrated web 165 and elastic member 166 configuration inhibits red-marking of the wearer's skin. Moreover, the illustrated leg and elastic barrier flap composite 46 provides a barrier flap portion 160 that looks soft (e.g., like a cushion) giving the wearer and/or the wearer's caregiver the perception that the training pant 20 is soft and comfortable to wear.

In the illustrated embodiment, the elastic members 166 are adhesively bonded to the inner and outer portions 194, 195 of the tubular element 167 of the barrier flap portions 160 of the leg and elastic barrier flap composites 46. It is understood, however, that the elastic members 166 can be operatively joined to the barrier flap portions 160 in any suitable manner as is well known in the art. It is also understood that the barrier flap portions 160 can include more or fewer elastic members 166 and that the elastic members can be any suitable elastomeric material (e.g., strands, ribbons).

In the illustrated embodiment, for example, each of the elastic members 166 is an elastic strand having a decitex of about 470. It is understood, however, that one or more of the elastic strands can have a different (i.e., greater or lesser) decitex than about 470. In the illustrated embodiment, the elastic strands are spaced from each other by about the same distance. It is understood, however, that the spacing between elastic strands can be varied. That is, the spacing between two of the elastic strands can be different than the spacing between two different elastic strands.

Figure 5A:
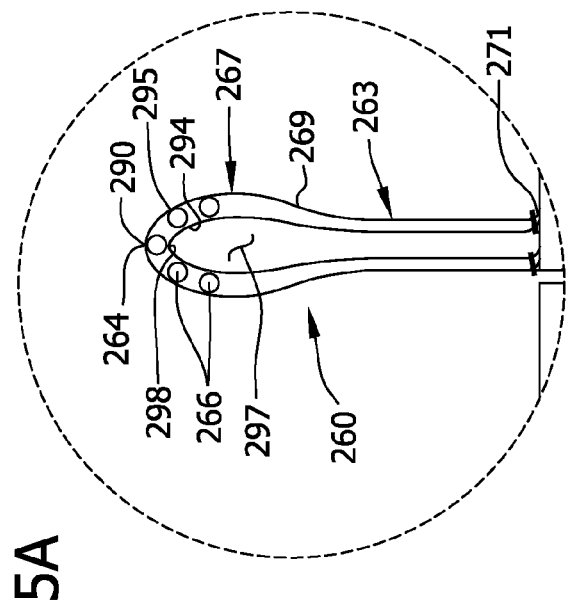
FIG. 5A is an enlarged view of a portion of one of the elastic barrier flaps illustrated in FIG. 5.
Figure 5:
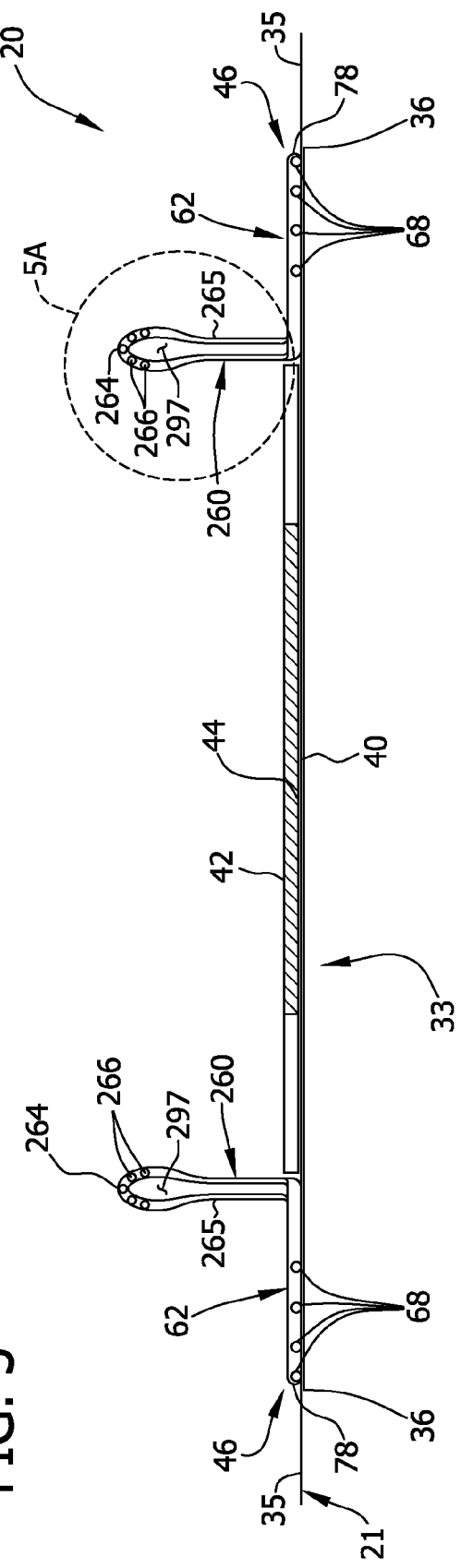
FIG. 5 is a cross-section similar to FIG. 3 but showing another embodiment of a pair of elastic barrier flaps.

Yet another suitable embodiment of a barrier flap portion 260 of the leg and elastic barrier flap composites 46 is illustrated in FIGS. 5 and 5A. The barrier flap portion 260 provides a barrier to the transverse flow of body exudates released by the wearer. More specifically, each of the barrier flap portions 260 assumes an upright configuration during use to define an unattached edge 264 in at least the crotch region 26 of the absorbent structure 33 of the training pant 20 to form a seal against the wearer's body.

As seen in FIGS. 5 and 5A, each of the barrier flap portions 260 of the leg and elastic barrier flap composites 46 comprises a web 265 and a plurality of elastic members 266 (five elastic members being illustrated in FIGS. 5 and 5A) operatively joined thereto. In this embodiment, the web 265 is formed from two pieces of material cooperatively defining a wall element, indicated generally at 263, and a tubular element, indicated generally at 267, extending upward from an upper end 269 of the wall element. In the illustrated embodiment, the other end or a lower end 271 of the wall element is affixed to the gasket portion 62 of the leg and elastic barrier flap composites 46. It is contemplated, however, that the lower end 271 of the wall element 263 can be affixed to the body-side liner 42 or outer cover 40 of the chassis 21 of the training pant 20.

As best illustrated in FIG. 5A, both the wall element 263 and the tubular element 267 include an inner portion 294 and an outer portion 295. The portion of the web 265 defining the outer portion 295 of the wall element 263 and tubular element 267 is bonded to and extends upward from the gasket portion 62 and is folded downward about a first fold line 290, which generally defines the unattached, distal edge 264 of the barrier flap portion 260. The outer portion 295 of the web 265 is then bonded again to the gasket portion 62 but at a location spaced from the other bond location.

The inner portion 294 of the web 265 extends upward from a bond point bonding the inner portion to the gasket portion 62 and is folded downward about a second fold line 298, which is generally aligned with and spaced below the first fold line 290. The inner portion 294 of the tubular element 267 is bonded to the gasket portion 62 at a bond point spaced from the other bond point location.

With reference still to FIG. 5A, each of the elastic members 266 are captured by or otherwise enclosed within the web 265. In the illustrated embodiment, the elastic members 266 are captured between the inner and outer portions 294, 295 of the tubular element 267. As seen in FIGS. 5 and 5A, one of the elastic members 266 is disposed generally adjacent the unattached, distal edge 264 of the barrier flap portion 260 and between the first and second fold lines 290, 298. The other elastic members 266 are positioned generally symmetrically downward and outward from the one adjacent the unattached, distal edge 264 in a generally inverse U-shaped pattern. The web 265 and the elastic members 266 cooperatively define a gap 297, which provides an air pocket (or air tunnel) within the barrier flap portion 260 of the leg and elastic barrier flap composites 46.

In this embodiment, the gap 297 extends between the wall element 263 and the tubular element 267 of the barrier flap portion 260. In the embodiments illustrated in FIGS. 3, 3A, 4 and 4A, the respective gaps 97, 197 were located exclusively within the tubular elements 67, 167. The wall elements 63, 163 of the earlier described embodiments were free from the respective gaps 97, 197.

In the embodiment illustrated in FIGS. 5 and 5A, the gap 297 extends at least through the crotch region 26 of the absorbent structure 33. More specifically, the gap 297 extends between the parts of the barrier flap portion 260 bonded in the front and back waist regions 22, 24 of the training pant 20. In other words, the gap 297 is formed in the parts of the barrier flap portion having the unattached, distal edge 264.

As a result, the web 265 and elastic member 266 configuration illustrated in FIGS. 5 and 5A provides a barrier flap portion 260 that is soft and comfortable for the wearer of the training pant 20. More specifically, the illustrated web 265 and elastic member 266 configuration inhibits red-marking of the wearer's skin. Moreover, the illustrated leg and elastic barrier flap composite 46 provides a barrier flap portion 260 that looks soft (e.g., like a cushion) giving the wearer and/or the wearer's caregiver the perception that the training pant 20 is soft and comfortable to wear.

In the illustrated embodiment, the elastic members 266 are adhesively bonded to the inner and outer portions 294, 295 of the tubular element 267 of the barrier flap portions 260 of the leg and elastic barrier flap composites 46. It is understood, however, that the elastic members 266 can be operatively joined to the barrier flap portions 260 in any suitable manner as is well known in the art. It is also understood that the barrier flap portions 260 can include more or fewer elastic members 266 and that the elastic members can be any suitable elastomeric material (e.g., strands, ribbons).

In the illustrated embodiment, for example, each of the elastic members 266 is an elastic strand having a decitex of about 470. It is understood, however, that one or more of the elastic strands can have a different (i.e., greater or lesser) decitex than about 470. In the illustrated embodiment, the elastic strands are spaced from each other by about the same distance. It is understood, however, that the spacing between elastic strands can be varied. That is, the spacing between two of the elastic strands can be different than the spacing between two different elastic strands.

Figure 6A:
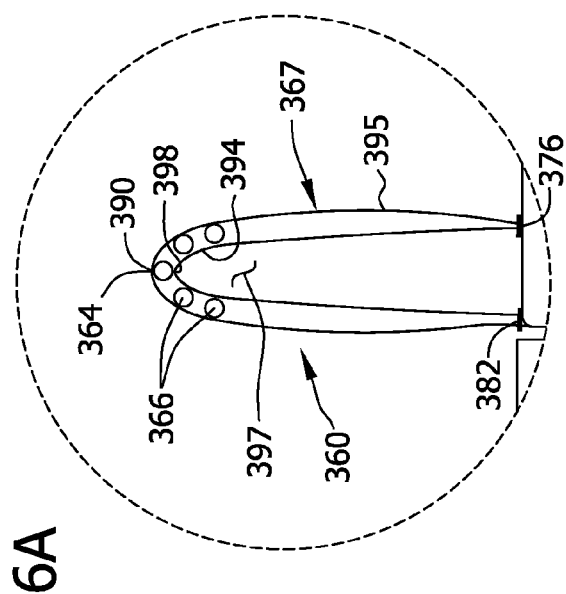
FIG. 6A is an enlarged view of a portion of one of the elastic barrier flaps illustrated in FIG. 6.
Figure 6:
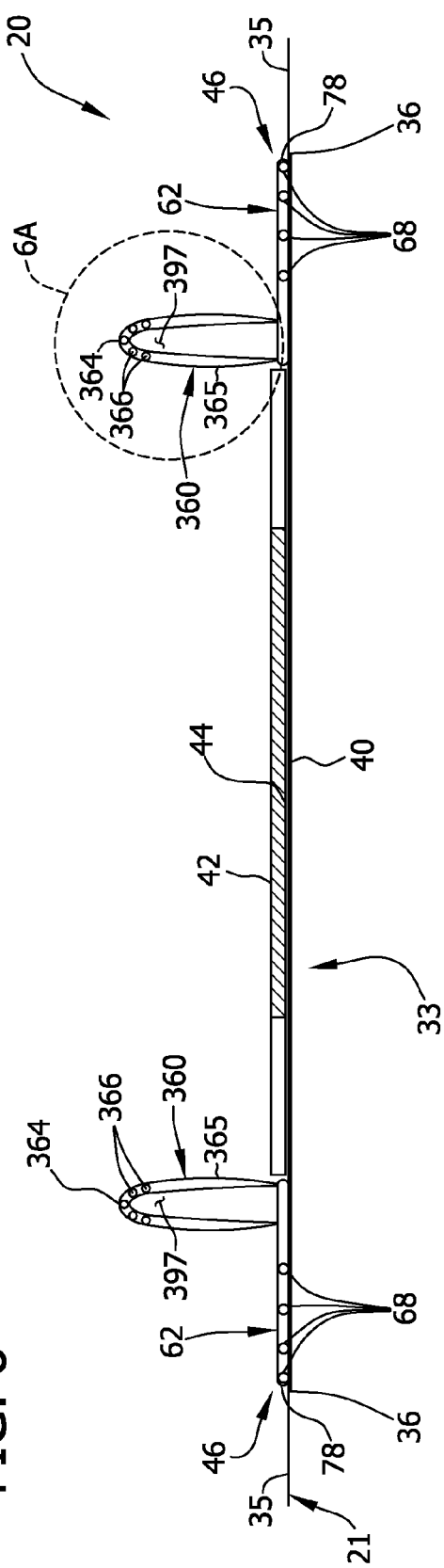
FIG. 6 is a cross-section similar to FIG. 3 but showing another embodiment of a pair of elastic barrier flaps.

Still another suitable embodiment of a barrier flap portion 360 of the leg and elastic barrier flap composites 46 is illustrated in FIGS. 6 and 6A. The barrier flap portion 360 provides a barrier to the transverse flow of body exudates released by the wearer. More specifically, each of the barrier flap portions 360 assumes an upright configuration during use to define an unattached edge 364 in at least the crotch region 26 of the absorbent structure 33 of the training pant 20 to form a seal against the wearer's body.

As seen in FIGS. 6 and 6A, each of the barrier flap portions 360 of the leg and elastic barrier flap composites 46 comprises a web 365 and a plurality of elastic members 366 (five elastic members being illustrated in FIGS. 6 and 6A) operatively joined thereto. In this embodiment, the web 365 is formed from two pieces of material which collectively define an arch, indicated generally at 367, extending upward from the gasket portion 62 of the leg and barrier flap composites 46.

As best illustrated in FIG. 6A, the arch 367 includes an inner portion 394 and an outer portion 395. The portion of the web 365 defining the outer portion 395 of the arch 367 is bonded to and extends upward from the gasket portion 62 and is folded downward about a first fold line 390, which generally defines the unattached, distal edge 364 of the barrier flap portion 260. The outer portion 395 of the web 365 is then bonded again to the gasket portion 62 but at a location spaced from the other bond location.

The inner portion 394 of the web 365 extends upward from a bond point 376 bonding the inner portion to the gasket portion 62 and is folded downward about a second fold line 398, which is generally aligned with and spaced below the first fold line 390. The inner portion 394 of the arch 367 is bonded to the gasket portion 62 at a bond point 382 spaced from the other bond point location.

With reference still to FIG. 6A, each of the elastic members 366 are captured by or otherwise enclosed within the web 365. In the illustrated embodiment, the elastic members 366 are captured between the inner and outer portions 394, 395 of the arch 367. As seen in FIGS. 6 and 6A, one of the elastic members 366 is disposed generally adjacent the unattached, distal edge 364 of the barrier flap portion 360 and between the first and second fold lines 390, 398. The other elastic members 366 are positioned generally symmetrically downward and outward from the one adjacent the unattached, distal edge 364 in a generally inverse U-shaped pattern. The web 365 and the elastic members 366 cooperatively define a gap 397, which provides an air pocket (or air tunnel) within the barrier flap portion 360 of the leg and elastic barrier flap composites 46. As seen in FIGS. 6 and 6A, the gap 397 is defined by the inner portion 394 of the arch 367 and a part of the gasket portion 62.

In the illustrated embodiment, the gap 397 extends at least through the crotch region 26 of the absorbent structure 33. More specifically, the gap 397 extends between the parts of the barrier flap portion 360 bonded in the front and back waist regions 22, 24 of the training pant 20. In other words, the gap 397 is formed in the parts of the barrier flap portion having the unattached, distal edge 364.

As a result, the web 365 and elastic member 366 configuration illustrated in FIGS. 6 and 6A provides a barrier flap portion 360 that is soft and comfortable for the wearer of the training pant 20. More specifically, the illustrated web 365 and elastic member 366 configuration inhibits red-marking of the wearer's skin. Moreover, the illustrated leg and elastic barrier flap composite 46 provides a barrier flap portion 360 that looks soft (e.g., like a cushion) giving the wearer and/or the wearer's caregiver the perception that the training pant 20 is soft and comfortable to wear.

In the illustrated embodiment, the elastic members 366 are adhesively bonded to the inner and outer portions 394, 395 of the arch 367 of the barrier flap portions 360 of the leg and elastic barrier flap composites 46. It is understood, however, that the elastic members 366 can be operatively joined to the barrier flap portions 360 in any suitable manner as is well known in the art. It is also understood that the barrier flap portions 360 can include more or fewer elastic members 366 and that the elastic members can be any suitable elastomeric material (e.g., strands, ribbons).

In the illustrated embodiment, for example, each of the elastic members 366 is an elastic strand having a decitex of about 470. It is understood, however, that one or more of the elastic strands can have a different (i.e., greater or lesser) decitex than about 470. In the illustrated embodiment, the elastic strands are spaced from each other by about the same distance. It is understood, however, that the spacing between elastic strands can be varied. That is, the spacing between two of the elastic strands can be different than the spacing between two different elastic strands.

Still yet another suitable embodiment of a barrier flap portion 460 of the leg and elastic barrier flap composites 46 is illustrated in FIGS. 7 and 7A. The barrier flap portion 460 provides a barrier to the transverse flow of body exudates released by the wearer. More specifically, each of the barrier flap portions 460 assumes an upright configuration during use to define an unattached edge 464 in at least the crotch region 26 of the absorbent structure 33 of the training pant 20 to form a seal against the wearer's body.

As seen in FIGS. 7 and 7A, each of the barrier flap portions 460 comprises a web 465 and a plurality of elastic members 466 (five elastic members being illustrated in FIGS. 7 and 7A) operatively joined thereto. In this embodiment, the web 465 is formed from two pieces of material which collectively define an arch, indicated generally at 467, extending upward from the gasket portion 62 of the leg and barrier flap composites 46.

As best illustrated in FIG. 7A, the arch 467 includes an inner portion 494 and an outer portion 495. The portion of the web 465 defining the outer portion 495 of the arch 467 is bonded to (e.g., a bond point 496) and extends upward from the gasket portion 62 and is folded downward about a first fold line 490, which generally defines the unattached, distal edge 464 of the barrier flap portion 460. The outer portion 495 of the arch 467 is then bonded again to the gasket portion 62 (e.g., a bond point 496') but at a location spaced from the other bond location.

The inner portion 494 of the arch 467 is bonded to the inner surface of the outer portion 495 at a pair of spaced-apart bond points 482, 482', which are spaced from the gasket portion 62. As seen in FIG. 7A, the inner portion 494 extends upward from one of the bond points 482 and is folded downward about a second fold line 498, which is generally aligned with and spaced below the first fold line 490, to the other bond point 482'.

With reference still to FIG. 7A, each of the elastic members 466 are captured by or otherwise enclosed within the web 465. In the illustrated embodiment, the elastic members 466 are captured between the inner and outer portions 494, 495 of the arch 467. As seen in FIGS. 7 and 7A, one of the elastic members 466 is disposed generally adjacent the unattached, distal edge 464 of the barrier flap portion 460 and between the first and second fold lines 490, 498. The other elastic members 466 are positioned generally symmetrically downward and outward from the one adjacent the unattached, distal edge 464 in a generally inverse U-shaped pattern. The web 465 and the elastic members 466 cooperatively define a gap 497, which provides an air pocket (or air tunnel) within the barrier flap portion 460 of the leg and elastic barrier flap composites 46. As seen in FIGS. 7 and 7A, the gap 497 is defined by the inner portion 494 of the arch 467 and a part of the gasket portion 62.

In the illustrated embodiment, the gap 497 extends at least through the crotch region 26 of the absorbent structure 33. More specifically, the gap 497 extends between the parts of the barrier flap portion 460 bonded in the front and back waist regions 22, 24 of the training pant 20. In other words, the gap 497 is formed in the parts of the barrier flap portion having the unattached, distal edge 464.

As a result, the web 465 and elastic member 466 configuration illustrated in FIGS. 7 and 7A provides a barrier flap portion 460 that is soft and comfortable for the wearer of the training pant 20. More specifically, the illustrated web 465 and elastic member 466 configuration inhibits red-marking of the wearer's skin. Moreover, the illustrated leg and elastic barrier flap composite 46 provides a barrier flap portion 460 that looks soft (e.g., like a cushion) giving the wearer and/or the wearer's caregiver the perception that the training pant 20 is soft and comfortable to wear.

In the illustrated embodiment, the elastic members 466 are adhesively bonded to the inner and outer portions 494, 495 of the arch 467 of the barrier flap portions 460 of the leg and elastic barrier flap composites 46. It is understood, however, that the elastic members 466 can be operatively joined to the barrier flap portions 460 in any suitable manner as is well known in the art.

It is also understood that the barrier flap portions 460 can include more or fewer elastic members 466 and that the elastic members can be any suitable elastomeric material (e.g., strands, ribbons). For example, an embodiment similar to the one illustrated in FIGS. 7 and 7A is illustrated in FIGS. 8 and 8A wherein a barrier flap portion 460 has three elastic members 466' captured between inner and outer portions 494, 495 of an arch 467.

In the embodiments illustrated in FIGS. 7, 7A, 8 and 8A, each of the elastic members 466, 466' is an elastic strand having a decitex of about 470. It is understood, however, that one or more of the elastic strands can have a different (i.e., greater or lesser) decitex than about 470. Moreover, in these embodiments, the elastic strands are spaced from each other by about the same distance.

Figure 9A:
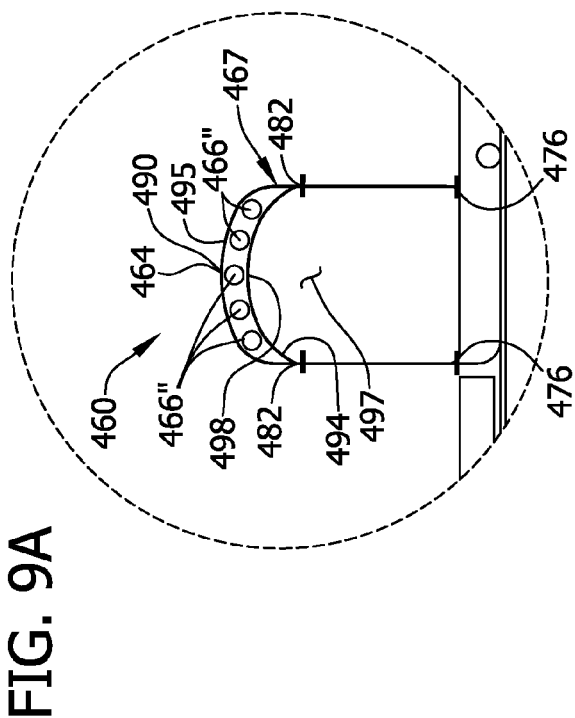
FIG. 9A is an enlarged view of a portion of one of the elastic barrier flaps illustrated in FIG. 9.
Figure 9:
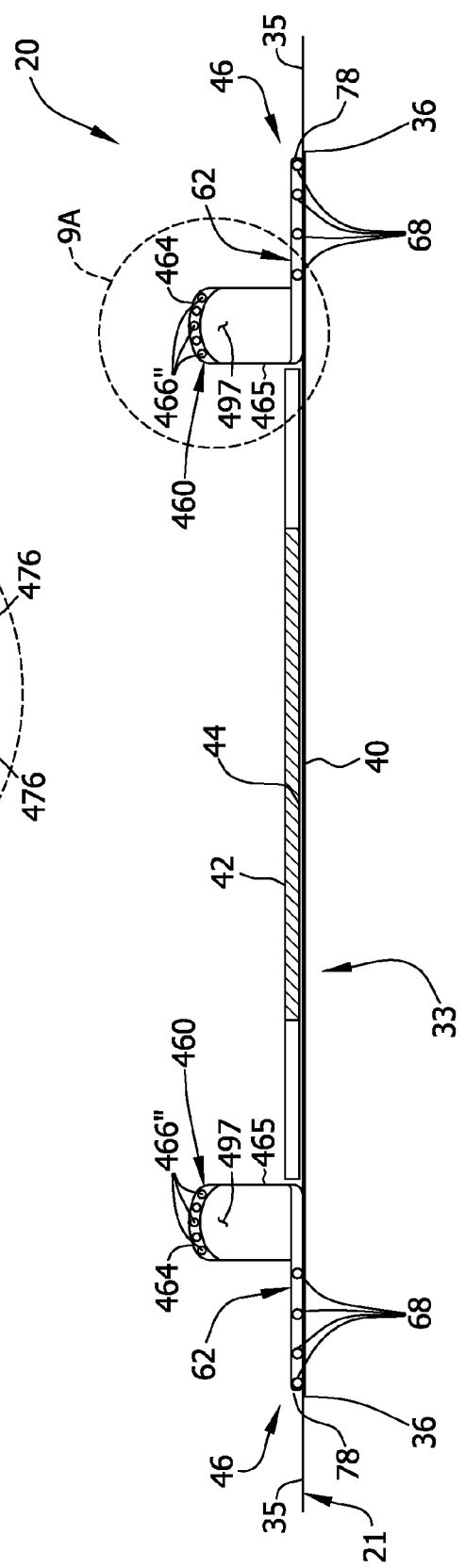
FIG. 9 is a cross-section similar to FIG. 3 but showing another embodiment of a pair of elastic barrier flaps.

However, FIGS. 9 and 9A illustrated embodiment similar to the ones illustrated in FIGS. 7, 7A, 8, and 8A except that each of the elastic strands 466" have a different decitex. In addition, the spacing between the elastic strands 466" is varied. That is, the spacing between the elastic strands 466" is not the same.

With reference again to FIG. 7A, each of the elastic members 466 are captured by or otherwise enclosed within the web 465. One of the elastic members 466 is disposed generally adjacent the unattached edge 464 of the barrier flap portion 460 and between the first and second fold lines 490, 498. The other elastic members 466 are positioned downward and outward from the one adjacent the unattached edge 464 in a generally inverse U-shaped pattern. The web 465 and elastic members 466 cooperatively define a gap 497, which provides an air pocket within the barrier flap portion 460 of the leg and elastic barrier flap composites 46.

As a result, the web 465 and elastic member 466 configuration illustrated in FIGS. 7 and 7A provides a barrier flap portion 460 that is soft and comfortable for the wearer of the training pant 20. More specifically, the illustrated web 465 and elastic member 466 configuration inhibits red-marking of the wearer's skin. Moreover, the illustrated leg and elastic barrier flap composite 446 provides a barrier flap portion 460 that looks soft (e.g., like a cushion) giving the wearer and/or the wearer's caregiver the perception that the training pant 20 is soft and comfortable to wear.

Another suitable embodiment of a barrier flap portion 560 of the leg and elastic barrier flap composites 46 is illustrated in FIGS. 10 and 10A. The barrier flap portion 560 provides a barrier to the transverse flow of body exudates released by the wearer. More specifically, each of the barrier flap portions 560 assumes an upright configuration during use to define an unattached edge 564 in at least the crotch region 26 of the absorbent structure 33 of the training pant 20 to form a seal against the wearer's body.

As seen in FIGS. 10 and 10A, each of the barrier flap portions 560 of the leg and elastic barrier flap composites 46 comprises a web 565 and a plurality of elastic members 566

(five elastic members being illustrated in FIGS. 10 and 10A) operatively joined thereto. In this embodiment, the web 565 is formed from two pieces of material which collectively define an arch, indicated generally at 567, extending upward from the gasket portion 62 of the leg and barrier flap composites 46.

As best illustrated in FIG. 10A, the arch 567 includes an inner portion 594 and an outer portion 595. The portion of the web 565 defining the outer portion 595 of the arch 567 is bonded to (e.g., at bond point 582) and extends upward from the gasket portion 62 and is folded downward about a first fold line 590, which generally defines the unattached, distal edge 564 of the barrier flap portion 560. The outer portion 595 of the web 565 is then bonded again to the gasket portion 62 at substantially the same location as the previous bond location (e.g., at bond point 582).

The inner portion 594 of the web 565 extends upward from the bond point 582, which bonds the inner portion to the gasket portion 62, and is folded downward about a second fold line 598, which is generally aligned with and spaced below the first fold line 590. The inner portion 594 of the arch 567 is then again bonded to the gasket portion 62 at the bond point 582.

With reference still to FIG. 10A, each of the elastic members 566 are captured by or otherwise enclosed within the web 565. In the illustrated embodiment, the elastic members 566 are captured between the inner and outer portions 594, 595 of the arch 567. As seen in FIGS. 10 and 10A, one of the elastic members 566 is disposed generally adjacent the unattached, distal edge 564 of the barrier flap portion 560 and between the first and second fold lines 590, 598. The other elastic members 566 are positioned generally symmetrically downward and outward from the one adjacent the unattached, distal edge 564 in a generally inverse U-shaped pattern. The web 565 and the elastic members 566 cooperatively define a gap 597, which provides an air pocket (or air tunnel) within the barrier flap portion 560 of the leg and elastic barrier flap composites 46. As seen in FIGS. 10 and 10A, the gap 597 is formed within the inner portion 594 of the arch 567.

In the illustrated embodiment, the gap 597 extends at least through the crotch region 26 of the absorbent structure 33. More specifically, the gap 597 extends between the parts of the barrier flap portion 560 bonded in the front and back waist regions 22, 24 of the training pant 20. In other words, the gap 597 is formed in the parts of the barrier flap portion having the unattached, distal edge 564.

As a result, the web 565 and elastic member 566 configuration illustrated in FIGS. 10 and 10A provides a barrier flap portion 560 that is soft and comfortable for the wearer of the training pant 20. More specifically, the illustrated web 565 and elastic member 566 configuration inhibits red-marking of the wearer's skin. Moreover, the illustrated leg and elastic barrier flap composite 46 provides a barrier flap portion 560 that looks soft (e.g., like a cushion) giving the wearer and/or the wearer's caregiver the perception that the training pant 20 is soft and comfortable to wear.

In the illustrated embodiment, the elastic members 566 are adhesively bonded to the inner and outer portions 594, 595 of the arch 567 of the barrier flap portions 560 of the leg and elastic barrier flap composites 46. It is understood, however, that the elastic members 566 can be operatively joined to the barrier flap portions 560 in any suitable manner as is well known in the art. It is also understood that the barrier flap portions 560 can include more or fewer elastic members 566 and that the elastic members can be any suitable elastomeric material (e.g., strands, ribbons).

In the illustrated embodiment, for example, each of the elastic members 566 is an elastic strand having a decitex of about 470. It is understood, however, that one or more of the elastic strands can have a different (i.e., greater or lesser) decitex than about 470. In the illustrated embodiment, the elastic strands are spaced from each other by about the same distance. It is understood, however, that the spacing between elastic strands can be varied. That is, the spacing between two of the elastic strands can be different than the spacing between two different elastic strands.

Another suitable embodiment of a barrier flap portion 660 of the leg and elastic barrier flap composites 46 is illustrated in FIGS. 11 and 11A. The barrier flap portion 660 provides a barrier to the transverse flow of body exudates released by the wearer. More specifically, each of the barrier flap portions 660 assumes an upright configuration during use to define an unattached edge 664 in at least the crotch region 26 of the absorbent structure 33 of the training pant 20 to form a seal against the wearer's body.

As seen in FIGS. 11 and 11A, each of the barrier flap portions 660 comprises a web 665 and a plurality of elastic members 666 (three elastic members being illustrated in FIGS. 11 and 11A) operatively joined thereto. In this embodiment, the web 665 is a single piece. As in some of the previous embodiments, the web 665 of this embodiment also forms the gasket portion 62 of the leg and elastic barrier flap composite 46. Thus, the single web 665 is used to form the entire leg and elastic barrier flap composite 46. It is understood, however, that the leg and elastic barrier flap composite 46 can be formed from one or more webs.

As best illustrated in FIG. 11A, the web 665 extends upward from the gasket portion 62 and is folded downward about a first fold line 690, which generally defines the unattached edge 664 of the barrier flap portion. A terminus 680 of the web 665 is bonded to the web at a point bond 682. In this embodiment, the web 665 defines a wall element, indicated generally at 663, and a tubular element, indicated generally at 667, extending upward from an upper end of the wall element. In the illustrated embodiment, the other end or a lower end of the wall element 663 is affixed to the gasket portion 62 of the leg and elastic barrier flap composites 46. It is contemplated, however, that the lower end of the wall element 663 can be affixed to the body-side liner 42 or outer cover 40 of the chassis 21 of the training pant 20. In this embodiment, the tubular element 667 of the web 665 defines an inner portion 694.

As seen in FIG. 11A, a cover (broadly, "an outer portion"), indicated generally at 699, covers and is bonded to the tubular element 667 such that the cover is spaced from the tubular element to define a gap 697, which provides an air pocket (or air tunnel) within the barrier flap portion 660 of the leg and elastic barrier flap composites 46. In the illustrated embodiment, the cover 699 is bonded to the tubular element 667 at a plurality of bond points 696.

In one suitable embodiment, the cover 699 is made from a soft, high loft nonwoven. For example, the cover 699 can be constructed of a spunbound-meltblown or a spunbound-meltblown-spunbound (SMS) having a basis weight of about 0.85 osy (about 28 gsm). In this example, both the meltblown and the spunbound layers can comprise polypropylene fibers. In another example, the cover 699 can be constructed of a bonded carded web (BCW) or a point bonded BCW. In yet another example, the cover 699 can be constructed of a through-air bonded carded web as described in U.S. Patent Application Publication No. 2005/0136773.

It is also contemplated that the cover 699 can be made from a nonwoven having generally soft fibers. In one configuration, the fibers are made from a generally soft material, made from a process that renders them soft, and/or or treated (either mechanically or chemically) to render them soft. Suitable soft materials include SFT315 polypropylene, which is available from ExxonMobil Chemical, and ASPUN fiber grade resins, which is available from The Dow Chemical Company. Processes for rendering the fibers of a nonwoven soft include, for example, creping and grooving. Treatment agents/additives for rendering the fiber of a nonwoven soft include, for example, fatty amides (e.g., erucamide). It is understood, however, that any suitable soft material can be used to make the cover 699.

In the illustrated embodiment, the gap 697 extends at least through the crotch region 26 of the absorbent structure 33. More specifically, the gap 697 extends between the parts of the barrier flap portion 660 bonded in the front and back waist regions 22, 24 of the training pant 20. In other words, the gap 697 is formed in the parts of the barrier flap portion having the unattached, distal edge 664.

As a result, the web 665, elastic member 666, and cover 699 are configured to provide a barrier flap portion 660 that is soft and comfortable for the wearer of the training pant 20. More specifically, the illustrated web 665, elastic member 666, and cover 699 configuration inhibits red-marking of the wearer's skin. Moreover, the illustrated leg and elastic barrier flap composite 46 provides a barrier flap portion 660 that looks soft (e.g., like a cushion) giving the wearer and/or the wearer's caregiver the perception that the training pant 20 is soft and comfortable to wear.

In the illustrated embodiment, the elastic members 666 are adhesively bonded to the web 665 forming the tubular element 667 of the barrier flap portions 660 of the leg and elastic barrier flap composites 46. It is understood, however, that the elastic members 666 can be operatively joined to the barrier flap portions 660 in any suitable manner as is well known in the art. It is also understood that the barrier flap portions 660 can include more or fewer elastic members 666 and that the elastic members can be any suitable elastomeric material (e.g., strands, ribbons).

Another suitable embodiment of a barrier flap portion 760 of the leg and elastic barrier flap composites 46 is illustrated in FIGS. 12 and 12A. The barrier flap portion 760 provides a barrier to the transverse flow of body exudates released by the wearer. More specifically, each of the barrier flap portions 760 assumes an upright configuration during use to define an unattached edge 764 in at least the crotch region 26 of the absorbent structure 33 of the training pant 20 to form a seal against the wearer's body.

As seen in FIGS. 12 and 12A, each of the barrier flap portions 760 comprises a web 765 and a plurality of elastic members 766 (two elastic members being illustrated in FIGS. 12 and 12A) operatively joined thereto. In this embodiment, the web 765 is a single piece. As in some of the previous embodiments, the web 765 of this embodiment also forms the gasket portion 62 of the leg and elastic barrier flap composite 46. Thus, the single web 765 is used to form the entire leg and elastic barrier flap composite 46. It is understood, however, that the leg and elastic barrier flap composite 46 can be formed from one or more webs.

As best illustrated in FIG. 12A, the web 765 extends upward from the gasket portion 62 and is folded downward about a first fold line 790, which generally defines the unattached edge 764 of the barrier flap portion. A terminus 780 of the web 665 is bonded to the web at a point bond 782. In this embodiment, the web 765 defines a wall element, indicated generally at 763, and a tubular element, indicated generally at 767, extending upward from an upper end of the wall element. In the illustrated embodiment, the other end or a lower end of the wall element 763 is affixed to the gasket portion 62 of the leg and elastic barrier flap composites 46. It is contemplated, however, that the lower end of the wall element 763 can be affixed to the body-side liner 42 or outer cover 40 of the chassis 21 of the training pant 20. In this embodiment, the tubular element 767 of the web 765 defines an inner portion 794.

As seen in FIG. 12A, a cover (broadly, "an outer portion"), indicated generally at 799, covers and is bonded to both the wall element 763 and the tubular element 767 such that the cover is spaced from the tubular element to define a gap 797, which provides an air pocket (or air tunnel) within the barrier flap portion 760 of the leg and elastic barrier flap composites 46. In the illustrated embodiment, the cover 799 is bonded to the tubular element 767.

In the illustrated embodiment, the gap 797 extends at least through the crotch region 26 of the absorbent structure 33. More specifically, the gap 797 extends between the parts of the barrier flap portion 760 bonded in the front and back waist regions 22, 24 of the training pant 20. In other words, the gap 797 is formed in the parts of the barrier flap portion having the unattached, distal edge 764.

As a result, the web 765, elastic member 766, and cover 799 are configured to provide a barrier flap portion 760 that is soft and comfortable for the wearer of the training pant 20. More specifically, the illustrated web 765, elastic member 766, and cover 799 configuration inhibits red-marking of the wearer's skin. Moreover, the illustrated leg and elastic barrier flap composite 46 provides a barrier flap portion 760 that looks soft (e.g., like a cushion) giving the wearer and/or the wearer's caregiver the perception that the training pant 20 is soft and comfortable to wear.

In the illustrated embodiment, the elastic members 766 are adhesively bonded to the web 765 forming the tubular element 767 of the barrier flap portions 760 of the leg and elastic barrier flap composites 46. It is understood, however, that the elastic members 766 can be operatively joined to the barrier flap portions 760 in any suitable manner as is well known in the art. It is also understood that the barrier flap portions 760 can include more or fewer elastic members 766 and that the elastic members can be any suitable elastomeric material (e.g., strands, ribbons).

Figure 13A:
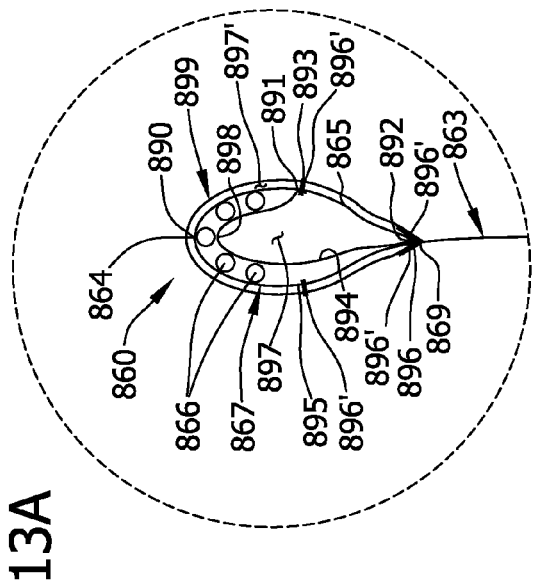
FIG. 13A is an enlarged view of a portion of one of the elastic barrier flaps illustrated in FIG. 13.
Figure 13:
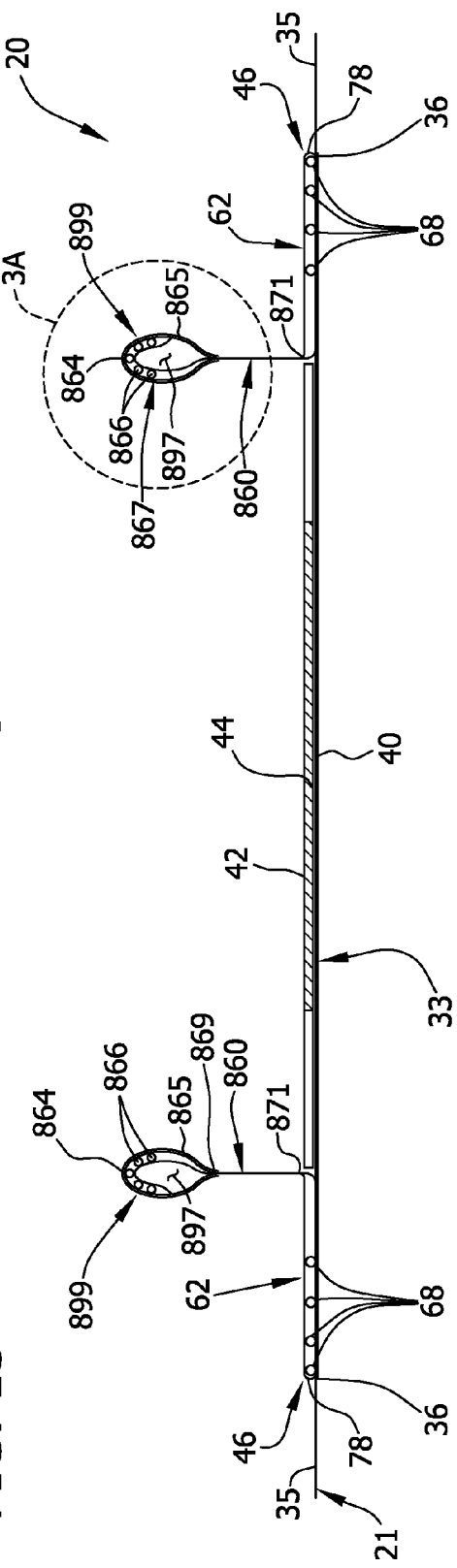
FIG. 13 is a cross-section similar to FIG. 3 but showing another embodiment of a pair of elastic barrier flaps.

Another suitable embodiment of a barrier flap portion 860 of the leg and elastic barrier flap composites 46 is illustrated in FIGS. 13 and 13A. The barrier flap portion 860 provides a barrier to the transverse flow of body exudates released by the wearer. More specifically, each of the barrier flap portions 860 assumes an upright configuration during use to define an unattached edge 864 in at least the crotch region 26 of the absorbent structure 33 of the training pant 20 to form a seal against the wearer's body.

As seen in FIG. 13A, each of the barrier flap portions 860 of the leg and elastic barrier flap composites 46 comprises a web 865 and a plurality of elastic members 866 (five elastic members being illustrated in FIGS. 13 and 13A) operatively joined thereto. In this embodiment, the web 865 is a single piece of material defining a wall element, indicated generally at 863, and a tubular element, indicated generally at 867, extending upward from an upper end 869 of the wall element. In the illustrated embodiment, the other end or a lower end 871 of the wall element is affixed to the gasket portion 62 of the leg and elastic barrier flap composites 46. It is contemplated, however, that the lower end 871 of the wall element 863 can be affixed to the body-side liner 42 or outer cover 40 of the chassis 21 of the training pant 20.

As best illustrated in FIG. 13A, the tubular element 867 includes an inner portion 894 and an outer portion 895. The portion of the web 865 defining the outer portion 895 of the tubular element 867 extends upward from the wall element 863 and is folded downward about a first fold line 890, which generally defines the unattached, distal edge 864 of the barrier flap portion 860. The web 865 is then folded inward and upward about a second fold line 892 and is bonded to itself via a bond point 896 generally at the second fold line 892. As see in FIG. 13A, the bond point 896 is located generally adjacent the upper end 869 of the wall element 863.

The inner portion 894 of the web 865 extends upward from the bond point 896 and folded downward about a third fold line 898, which is generally aligned with and spaced below the first fold line 890. A terminus 891 of the inner portion 894 of the tubular element 867 is bonded to the outer portion 895 of the tubular element web at a point bond 893. It is contemplated that the web 65 can be made from more than one-piece of material. For example, the inner portion 894 and/or the outer portion 895 of the web 865 can be formed as a separate piece and bonded to other portions of the web.

With reference still to FIG. 13A, each of the elastic members 866 are captured by or otherwise enclosed within the web 865. In the illustrated embodiment, the elastic members 866 are captured between the inner and outer portions 894, 895 of the tubular element 867. As seen in FIGS. 13 and 13A, one of the elastic members 866 is disposed generally adjacent the unattached, distal edge 864 of the barrier flap portion 860 and between the first and third fold lines 890, 898. The other elastic members 866 are positioned generally symmetrically downward and outward from the one adjacent the unattached, distal edge 864 in a generally inverse U-shaped pattern. The web 865 and the elastic members 866 cooperatively define a gap 897, which provides an air pocket (or air tunnel) within the barrier flap portion 860 of the leg and elastic barrier flap composites 46.

As seen in FIG. 13A, a cover (broadly, "an outer portion"), indicated generally at 899, covers and is bonded to the tubular element 867 such that the cover is spaced from the tubular element to define a gap 897', which provides a second air pocket (or air tunnel) within the barrier flap portion 860 of the leg and elastic barrier flap composites 46. In the illustrated embodiment, the cover 899 is bonded to the tubular element 867 at a plurality of bond points 896'.

In the illustrated embodiment, the gap 897 extends at least through the crotch region 26 of the absorbent structure 33. More specifically, the gap 897 extends between the parts of the barrier flap portion 860 bonded in the front and back waist regions 22, 24 of the training pant 20. In other words, the gap 897 is formed in the parts of the barrier flap portion having the unattached, distal edge 864.

As a result, the web 865 and elastic member 866 configuration illustrated in FIGS. 13 and 13A provides a barrier flap portion 860 that is soft and comfortable for the wearer of the training pant 20. More specifically, the illustrated web 865 and elastic member 866 configuration inhibits red-marking of the wearer's skin. Moreover, the illustrated leg and elastic barrier flap composite 846 provides a barrier flap portion 860 that looks soft (e.g., like a cushion) giving the wearer and/or the wearer's caregiver the perception that the training pant 20 is soft and comfortable to wear.

In the illustrated embodiment, the elastic members 866 are adhesively bonded to the inner and outer portions 894, 895 of the tubular element 867 of the barrier flap portions 860 of the leg and elastic barrier flap composites 46. It is understood, however, that the elastic members 866 can be operatively joined to the barrier flap portions 860 in any suitable manner as is well known in the art. It is also understood that the barrier flap portions 860 can include more or fewer elastic members 866 and that the elastic members can be any suitable elastomeric material (e.g., strands, ribbons).

In the illustrated embodiment, for example, each of the elastic members 866 is an elastic strand having a decitex of about 470. It is understood, however, that one or more of the elastic strands can have a different (i.e., greater or lesser) decitex than about 470. In the illustrated embodiment, the elastic strands are spaced from each other by about the same distance. It is understood, however, that the spacing between elastic strands can be varied. That is, the spacing between two of the elastic strands can be different than the spacing between two different elastic strands.

Figure 14A:
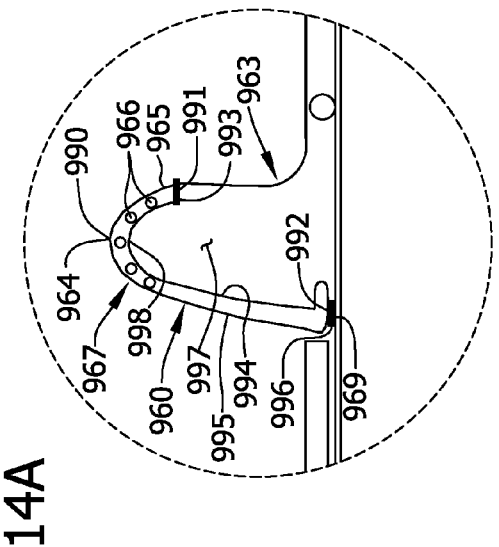
FIG. 14A is an enlarged view of a portion of one of the elastic barrier flaps illustrated in FIG. 14.
Figure 14:
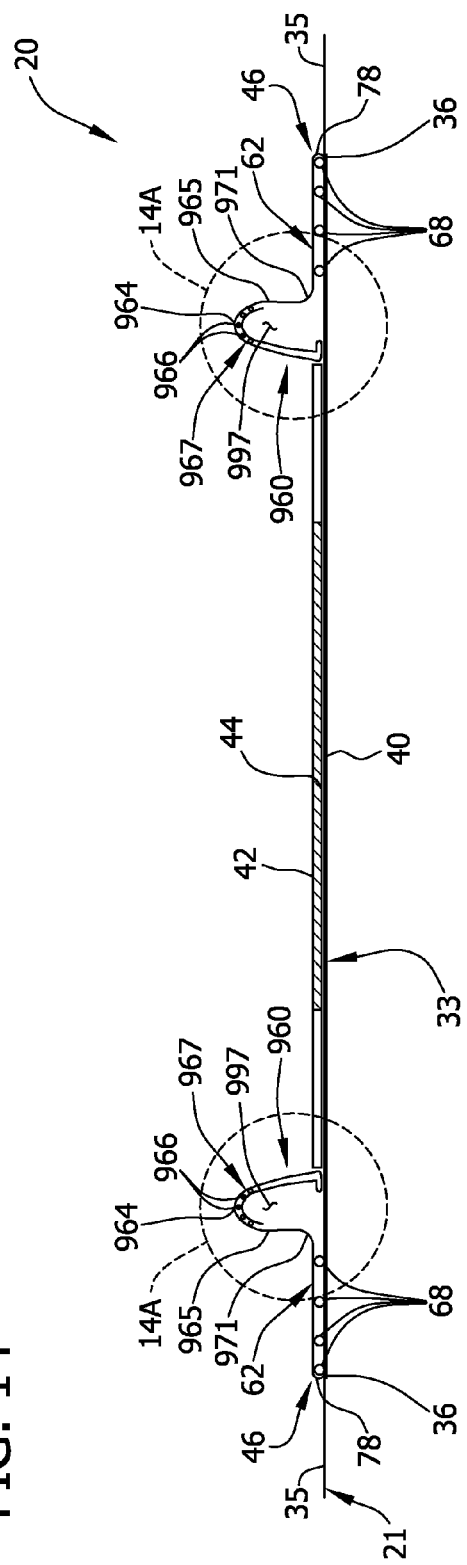
FIG. 14 is a cross-section similar to FIG. 3 but showing yet another embodiment of a pair of elastic barrier flaps.

Another suitable embodiment of a barrier flap portion 960 of the leg and elastic barrier flap composites 46 is illustrated in FIGS. 14 and 14A. The barrier flap portion 960 provides a barrier to the transverse flow of body exudates released by the wearer. More specifically, each of the barrier flap portions 960 assumes an upright configuration during use to define an unattached edge 964 in at least the crotch region 26 of the absorbent structure 33 of the training pant 20 to form a seal against the wearer's body.

As seen in FIGS. 14 and 14A, each of the barrier flap portions 960 comprises a web 965 and a plurality of elastic members 966 (five elastic members being illustrated in FIGS. 14 and 14A) operatively joined thereto. In this embodiment, the web 965 is formed from a single piece of material configured to define an arch, indicated generally at 967, extending upward from the gasket portion 62 of the leg and barrier flap composites 46.

As best illustrated in FIG. 14A, the arch 967 includes an inner portion 994 and an outer portion 995. The portion of the web 965 defining the outer portion 995 of the arch 967 is bonded to (e.g., a bond point 996) and extends upward from the gasket portion 62 and is folded downward about a first fold line 990, which generally defines the unattached, distal edge 964 of the barrier flap portion 960. The inner portion 994 of the arch 967 is bonded to the inner surface of the outer portion 995 at a bond point 991. As seen in FIG. 14A, the inner portion 994 extends upward from the bond point 991 and is folded downward about a second fold line 998, which is generally aligned with and spaced below the first fold line 990.

With reference still to FIG. 14A, each of the elastic members 966 are captured by or otherwise enclosed within the web 965. In the illustrated embodiment, the elastic members 966 are captured between the inner and outer portions 994, 995 of the arch 967. As seen in FIGS. 14 and 14A, one of the elastic members 966 is disposed generally adjacent the unattached, distal edge 964 of the barrier flap portion 960 and between the first and second fold lines 990, 998. The other elastic members 966 are positioned generally symmetrically downward and outward from the one adjacent the unattached, distal edge 964 in a generally inverse U-shaped pattern. The web 965 and the elastic members 966 cooperatively define a gap 997, which provides an air pocket (or air tunnel) within the barrier flap portion 960 of the leg and elastic barrier flap composites 46. As seen in FIGS. 14 and 14A, the gap 997 is defined by the inner portion 994 of the arch 967 and a part of the outer cover 40.

In the illustrated embodiment, the gap 997 extends at least through the crotch region 26 of the absorbent structure 33. More specifically, the gap 997 extends between the parts of the barrier flap portion 960 bonded in the front and back waist regions 22, 24 of the training pant 20. In other words, the gap 997 is formed in the parts of the barrier flap portion having the unattached, distal edge 964.

As a result, the web 965 and elastic member 466 configuration illustrated in FIGS. 14 and 14A provides a barrier flap portion 960 that is soft and comfortable for the wearer of the training pant 20. More specifically, the illustrated web 965 and elastic member 966 configuration inhibits red-marking of the wearer's skin. Moreover, the illustrated leg and elastic barrier flap composite 46 provides a barrier flap portion 960 that looks soft (e.g., like a cushion) giving the wearer and/or the wearer's caregiver the perception that the training pant 20 is soft and comfortable to wear.

Figure 15:
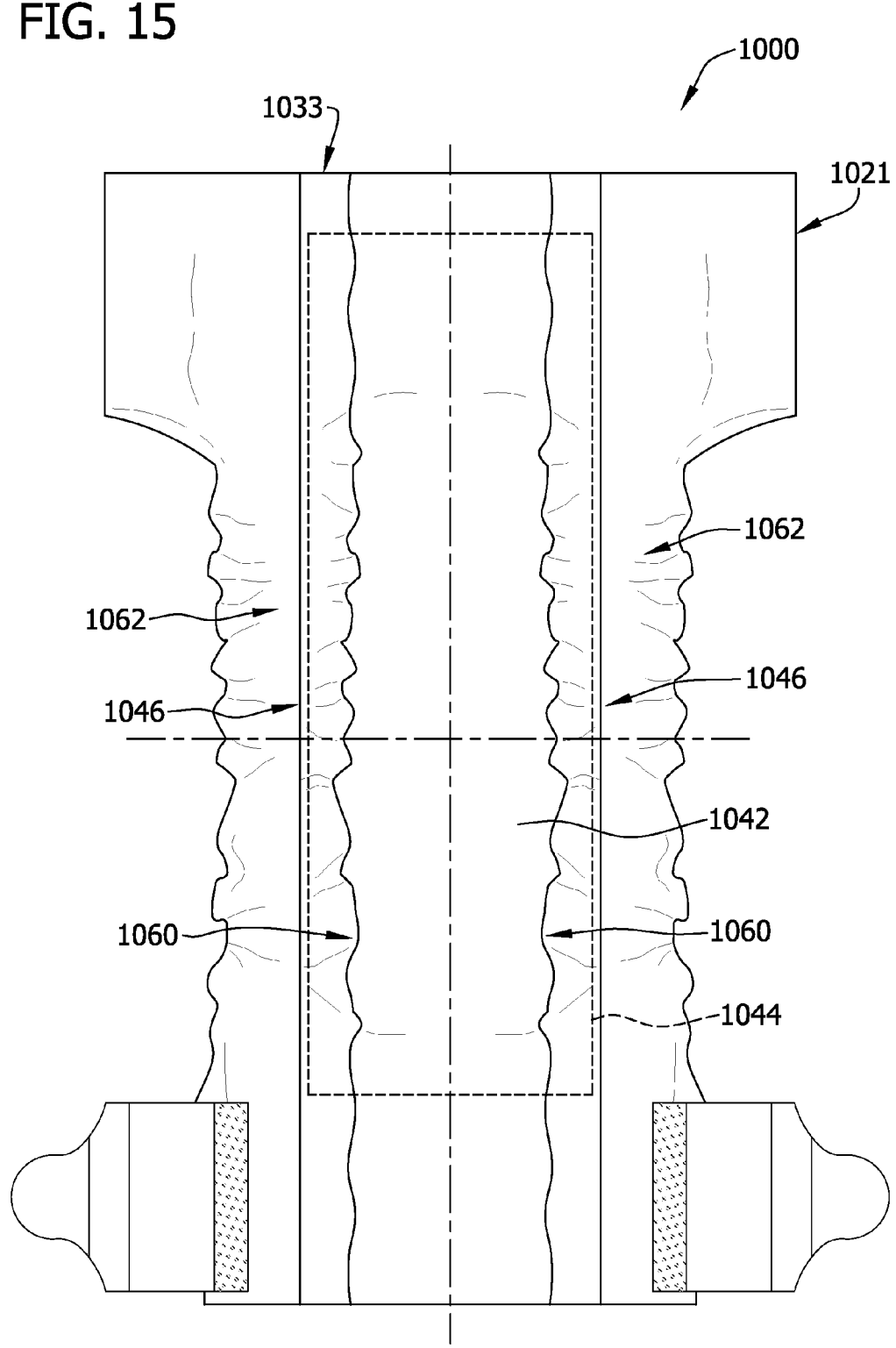
FIG. 15 is a top plan view of one embodiment of an absorbent article in the form of a diaper being in an unfastened, unfolded and laid flat condition, and showing the surface of the diaper that faces a wearer during use.
Figure 16:
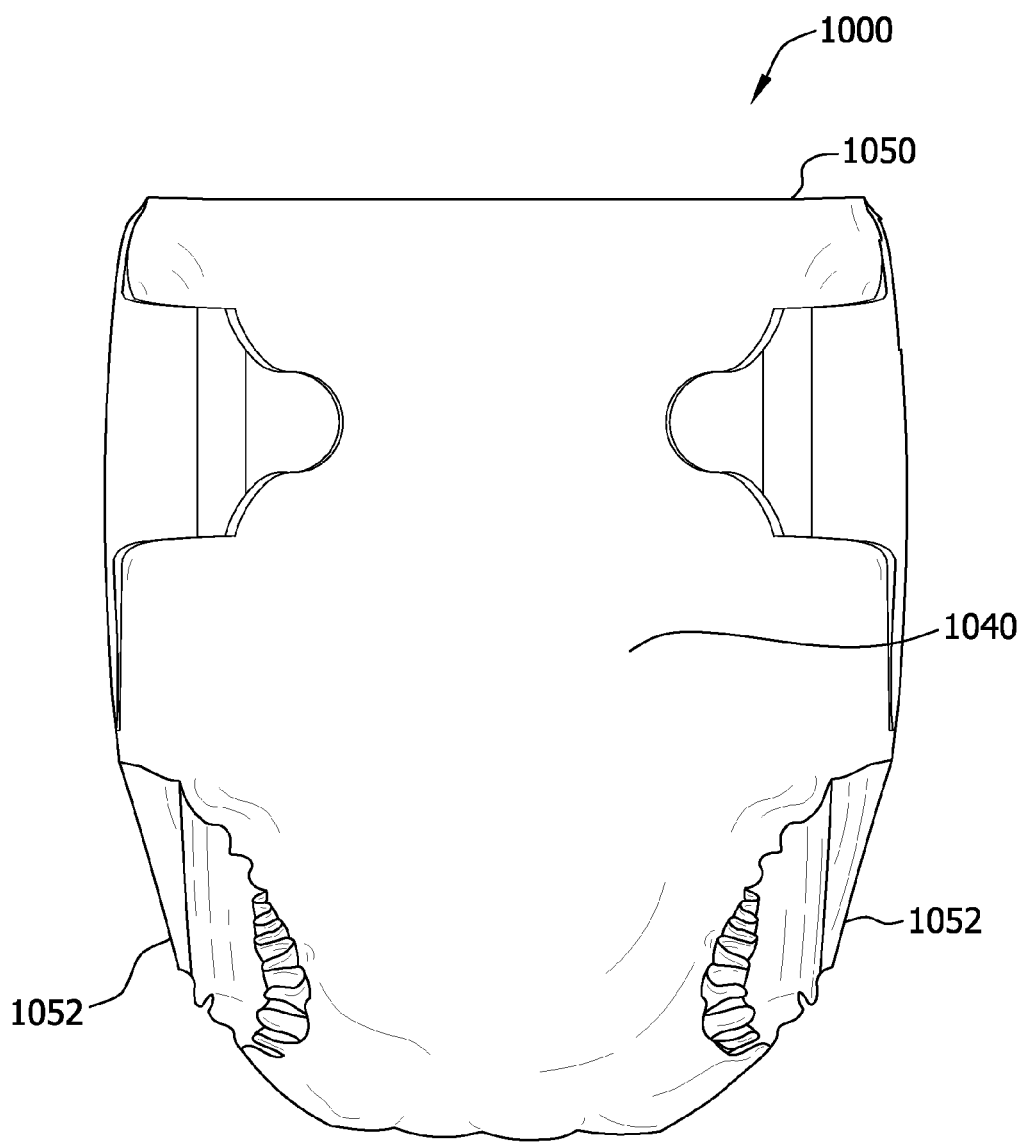
FIG. 16 is a front perspective of the diaper of FIG. 15 in a wear configuration of the diaper.

FIG. 15 illustrates an absorbent article in the form of a diaper in an unfastened, unfolded and laid-flat condition and indicated generally by reference number 1000. FIG. 16 illustrates the diaper 1000 in a wear configuration. The diaper 1000 comprises a chassis, indicated at 1021, having a generally rectangular absorbent structure, indicated at 1033. The absorbent structure 1033 of the diaper 1000 is configured to contain and/or absorb exudates released by a wearer of the training pant. As seen in FIGS. 15 and 16, the illustrated absorbent structure 1033 comprises an outer cover 1040, a body-side liner 1042, and an absorbent assembly 1044 disposed between the outer cover and the body-side liner. In the wear configuration of the diaper 1000, which is illustrated in FIG. 16, the diaper has a waist opening 1050 and a pair of leg openings 1052.

As seen in FIG. 15, the diaper 1000 includes a pair of spaced-apart leg and elastic barrier flap composites 1046. Each of the leg and elastic barrier flap composites 1046 has a barrier flap portion, indicated generally at 1060, and a gasket portion, indicated generally at 1062. In the illustrated embodiment, the leg and elastic barrier flap composites 1046 are substantially the same as the leg and elastic barrier flap composites 46 of FIGS. 1-3B. It is contemplated, however, that diaper 1000 can include any of the leg and elastic barrier flap composites shown and described herein.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Moreover, the use of "top", "bottom", "above", "below" and variations of these terms is made for convenience, and does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. An elastic barrier flap for providing a barrier to transverse flow of body exudates released by a wearer in an absorbent article, the barrier flap comprising an outer portion, an inner portion disposed within the outer portion, an air tunnel defined at least in part by the inner portion, a plurality of elastic members captured between the inner and outer portions, and a covering for covering at least a portion of the outer portion such that a second air tunnel is defined at least in part by a gap between the covering and the outer portion.

2. The elastic barrier flap of claim 1 wherein the plurality of elastic members are arranged symmetrically about the gap defined by the inner portion.

3. The elastic barrier flap of claim 2 wherein the plurality of elastic members are arranged in a generally inverse U-shaped pattern.

4. The elastic barrier flap of claim 1 wherein the outer portion defines a wall element, and the inner and outer portions cooperatively define a tubular element extending upward from the wall element, wherein the gap is defined at least in part by the tubular element.

5. The elastic barrier flap of claim 4 wherein the plurality of elastic members being disposed in the tubular element.

6. The elastic barrier flap of claim 1 wherein the inner and outer portions collectively define an arch.

7. The elastic barrier flap of claim 1 wherein the inner and outer portions are formed by separate pieces of material.

8. The elastic barrier flap of claim 1, wherein the elastic members are adhesively bonded to the inner and outer portions of the barrier flap.

9. The elastic barrier flap of claim 1, wherein the elastic members comprise elastic strands.

10. The elastic barrier flap of claim 9, wherein the elastic strands have a decitex of greater than 470.

11. The elastic barrier flap of claim 1, wherein the barrier flap comprises a nonwoven laminate.

12. The elastic barrier flap of claim 11, wherein the laminate comprises at least one fine fiber component layer and at least one continuous filament layer.

13. The elastic barrier flap of claim 12, wherein the fine fiber layer includes fibers having an average diameter of up to 10 microns.

14. The elastic barrier flap of claim 12, wherein the fine fiber layer includes fibers having a basis weight of from 1.5 gsm to 26 gsm.

15. The elastic barrier flap of claim 12, wherein the continuous filament layer includes filaments with an average diameter of from 12 microns to 22 microns.

16. The elastic barrier flap of claim 12, wherein the continuous filament layer includes filaments having a basis weight of from 10 gsm to 30 gsm.

17. The elastic barrier flap of claim 12, wherein the at least one fine fiber component layer and the at least one continuous filament layer are bonded together.

18. An absorbent article comprising an outer cover, a body-side liner, an absorbent assembly disposed between the outer cover and the body-side liner, and a pair of the elastic barrier flaps of claim 1.

19. The absorbent article of claim 18, further comprising a front waist region, a back waist region, and a crotch region extending between and interconnecting the front and back waist regions, the plurality of elastic members of each of the elastic barrier flaps being adapted to be spaced from the body-side liner in at least the crotch region during use.

20. The absorbent article of claim 18, wherein the body-side liner comprises a nonwoven polypropylene material.

* * * * *